(12) United States Patent
Hopkins et al.

(10) Patent No.: US 9,301,540 B2
(45) Date of Patent: Apr. 5, 2016

(54) PREBIOTIC COMPOSITION AND METHODS OF MAKING AND USING THE SAME

(75) Inventors: Anne Chace Hopkins, Diboll, TX (US);
Thomas A. Lehtinen, Diboll, TX (US);
Matthew W. Lowe, Lufkin, TX (US);
Xuerong Wang, Nacogdoches, TX (US);
Wilton Hays Killam, Jr., Lufkin, TX (US)

(73) Assignee: Georgia-Pacific Panel Products LLC, Atlanta, GA (US)

( * ) Notice: Subject to any disclaimer, the term of this patent is extended or adjusted under 35 U.S.C. 154(b) by 0 days.

(21) Appl. No.: 12/480,171

(22) Filed: Jun. 8, 2009

(65) Prior Publication Data
US 2009/0304852 A1    Dec. 10, 2009

Related U.S. Application Data

(60) Provisional application No. 61/059,960, filed on Jun. 9, 2008, provisional application No. 61/121,005, filed on Dec. 9, 2008.

(51) Int. Cl.
*A23K 1/16*   (2006.01)
*A23K 1/00*   (2006.01)
(Continued)

(52) U.S. Cl.
CPC . *A23K 1/188* (2013.01); *A23K 1/12* (2013.01); *A23K 1/146* (2013.01); *A23K 1/1643* (2013.01); *A23K 1/1646* (2013.01); *A23K 1/1813* (2013.01); *A23L 1/0528* (2013.01); *A23L 1/0534* (2013.01); *A23L 1/3002* (2013.01); *A23L 1/3082* (2013.01)

(58) Field of Classification Search
CPC ....... A23K 1/12; A23K 1/1643; A23K 1/188; A23K 1/1646; A23K 1/146; A23K 1/1813; A23L 1/0528; A23L 1/3082; A23L 1/3002; A23L 1/0534
USPC .......................... 426/71, 2, 425, 655; 514/54
See application file for complete search history.

(56) References Cited

U.S. PATENT DOCUMENTS 2,453,142 A * 11/1948 Lee ............................... 426/616
3,733,405 A    5/1973 Derrig
(Continued)

FOREIGN PATENT DOCUMENTS

EP    0143490 A2    6/1985
EP    1407037 B1    1/2006
(Continued)

OTHER PUBLICATIONS

Ebringerov et al, International Journal of Biological Macromolecules 42 (2008) p. 1-5 (published online Aug. 2, 2007).*
(Continued)

*Primary Examiner* — Erik Kashnikow
*Assistant Examiner* — Assaf Zilbering
(74) *Attorney, Agent, or Firm* — Ram W. Sabnis

(57) ABSTRACT

A prebiotic composition comprising soluble extractable material from a lignocellulosic source. A method of producing a composition, comprising providing a lignocellulosic source; extracting soluble materials from the lignocellulosic source to produce soluble extractable material; and processing the soluble extractable material to yield a prebiotic composition, wherein the prebiotic composition comprises hemicellulose and exhibits prebiotic activity.

8 Claims, 8 Drawing Sheets

(51) Int. Cl.

| | |
|---|---|
| A23L 1/308 | (2006.01) |
| A61K 31/715 | (2006.01) |
| A61K 31/736 | (2006.01) |
| A23K 1/18 | (2006.01) |
| A23L 1/30 | (2006.01) |
| A23K 1/14 | (2006.01) |
| A23L 1/0534 | (2006.01) |
| A23K 1/12 | (2006.01) |
| A23L 1/0528 | (2006.01) |

(56) References Cited

U.S. PATENT DOCUMENTS

| | | | |
|---|---|---|---|
| 3,796,797 | A | 3/1974 | Parish et al. |
| 3,878,298 | A | 4/1975 | Parish et al. |
| 3,988,483 | A | 10/1976 | Deyoe et al. |
| 4,820,527 | A * | 4/1989 | Christensen et al. ............ 426/2 |
| 5,756,098 | A | 5/1998 | Price et al. |
| 6,087,092 | A | 7/2000 | Richards |
| 6,241,983 | B1 | 6/2001 | Paul et al. |
| 6,783,780 | B1 | 8/2004 | De Jong et al. |
| 7,048,937 | B2 | 5/2006 | Dawson et al. |
| 7,109,005 | B2 | 9/2006 | Eroma et al. |
| 7,291,607 | B2 | 11/2007 | Day et al. |
| 7,625,728 | B2 | 12/2009 | Eroma et al. |
| 7,638,151 | B2 | 12/2009 | Duan et al. |
| 7,772,212 | B2 | 8/2010 | Day et al. |
| 8,828,970 | B2 | 9/2014 | Lowe et al. |
| 2003/0162300 | A1 | 8/2003 | Kunz et al. |
| 2004/0091537 | A1 | 5/2004 | Miller |
| 2004/0175460 | A1 | 9/2004 | Zenovich |
| 2004/0176320 | A1 | 9/2004 | Natunen et al. |
| 2005/0064447 | A1 | 3/2005 | Huang |
| 2005/0079244 | A1 | 4/2005 | Giffard et al. |
| 2005/0288250 | A1 | 12/2005 | Rautonen et al. |
| 2006/0034978 | A1 | 2/2006 | Deem et al. |
| 2006/0051812 | A1 | 3/2006 | Helin et al. |
| 2006/0068022 | A1 | 3/2006 | Playford |
| 2006/0182708 | A1 | 8/2006 | Bockmuhl et al. |
| 2007/0141678 | A1 | 6/2007 | Green et al. |
| 2007/0196890 | A1 | 8/2007 | Vulevic et al. |
| 2007/0243268 | A1 | 10/2007 | Jaffe |
| 2007/0298014 | A1 | 12/2007 | Huang |
| 2008/0138862 | A1 * | 6/2008 | Felby et al. ............ 435/72 |
| 2008/0226603 | A1 | 9/2008 | Al-Ghazzewi et al. |
| 2009/0004327 | A1 | 1/2009 | Duan et al. |
| 2010/0028485 | A1 | 2/2010 | Tuohy et al. |
| 2010/0056472 | A1 | 3/2010 | Duan et al. |
| 2013/0018015 | A1 | 1/2013 | Hopkins et al. |
| 2014/0378412 | A1 | 12/2014 | Lowe et al. |

FOREIGN PATENT DOCUMENTS

| | | | |
|---|---|---|---|
| EP | 2025242 | A1 | 2/2009 |
| GB | 2404561 | A | 2/2005 |
| JP | 2001226409 | A | 8/2001 |
| JP | 2004229607 | A | 8/2004 |
| JP | 2005027541 | A | 2/2005 |
| JP | 4078778 | B2 | 4/2008 |
| KR | 1019910004110 | A | 3/1991 |
| KR | 100597659 | B1 | 6/2006 |
| WO | 0033854 | A1 | 6/2000 |
| WO | 03015533 | A1 | 2/2003 |
| WO | 04000340 | A2 | 12/2003 |
| WO | 2005111195 | A2 | 11/2005 |
| WO | 2005111195 | A3 | 11/2005 |
| WO | 2007091231 | A1 | 8/2007 |
| WO | 2009117790 | A2 | 10/2009 |
| WO | 2009152089 | A2 | 12/2009 |
| WO | 2009152089 | A3 | 12/2009 |
| WO | 2010089453 | A1 | 8/2010 |
| WO | 2011031531 | A2 | 3/2011 |
| WO | 2011031531 | A3 | 3/2011 |
| WO | 2011072051 | A2 | 6/2011 |
| WO | 2011072051 | A3 | 6/2011 |

OTHER PUBLICATIONS

Pietarinen et al., Knotwood and bark extracts: strong antioxidants from waste materials, J Wood Sci (2006) 52: pp. 436-444 (Mar. 15, 2006).*

Mandre et al., The Quality of Stemwood of Pinus sylvestris in an Alkalised Environment, Water Air Soil Pollut (2007) 182: pp. 163-172 (Jan. 9, 2007).*

Production of hemicellulosic sugars from Pinus pinaster wood by sequential steps of aqueous extraction and acid hydrolysis, Gonzalez-Munoz et al., 46 Wood Sci Technol (Feb. 24, 2011) p. 271-285.*

Kenealy et al., Vapor-phase diethyl oxalate pretreatment of wood chips Part 2 Release of hemicellulosic carbohydrates, Holzforschung, vol. 61, pp. 230-235 (2007).*

Nabarlatz, Debora Alcida, "Autohydrolysis of agricultural by-products for the production of xylo-oligosaccharides," Dissertation, Departament d'Enginyeria Quimica, Universitat Rovira I Virgili, Sep. 29, 2006, pp. 1-4, 19-22, cover page, Tarragona.

Nacos, M. K., et al., "Kenaf xylan—a source of biologically active acidic oligosaccharides," Carbohydrate Polymers, 2006, vol. 66, issue 1, pp. 126-134, Elsevier Ltd.

Allision, Milton J., et al., "*Synergistes jonesii*, gen. nov., sp. nov.: A rumen bacterium that degrades toxic pyridinediols," System. Appl. Microbiol., 1992, pp. 522-529, vol. 15, Gustax Fischer Verlag, Stuttgart/ NewYork.

Bar-Shavit, Zvi, et al., "Mannose-binding activity of *Escherichia coli*: a determinant of attachment and ingestion of the bacteria by macrophages," Aug. 1980, pp. 417-424, vol. 29, No. 2, Infection and Immunity.

Chaney, Albert L., et al., "Modified reagents for determination of urea and ammonia," 1962, pp. 130-132, vol. 8, No. 2, Clinical Chemistry.

Foreign communication from a related counterpart application—International Search Report and Written Opinion, PCT/US2009/046605, Jan. 20, 2010, 7 pages.

Gedek, B. R., "Adherence of *Escherichia coli* serogroup 0 157 and the Salmonella Typhimurium mutant DT 104 to the surface of *Saccharomyces boulardii*," Mycoses, 1999, pp. 261-264 plus 1 page publishing information, vol. 42, © 2002 EBSCO Publishing.

Jouany, Jean-Pierre, "Rumen microbial metabolism and ruminant digestion," 1991, pp. 217-237 plus 2 pages cover and publishing information, INRA Editions, Paris.

Mirelman, David, et al., "Screening of bacterial isolates for mannose-specific lectin activity by agglutination of yeasts," Apr. 1980, pp. 328-331, vol. 11, No. 4, Journal of Clinical Microbiology.

Provisional patent application entitled "Natural prebiotic derived from southern yellow pine polysaccharides," by Tom Lehtinen, et al., filed Dec. 9, 2008 as U.S. Appl. No. 61/121,005.

Provisional patent application entitled "Oligosaccharide prebiotic product processed from softwood molasses," by Tom Lehtinen, et al., filed Jun. 9, 2008 as U.S. Appl. No. 61/059,960.

Provisional patent application entitled "Ruminant gas reduction composition and methods of making and using the same," by Matthew W. Lowe, et al., filed Aug. 27, 2009 as U.S. Appl. No. 61/237,396.

Provisional patent application entitled "Nutritional composition and methods of making and using same," by Anne Chase Hopkins, et al., filed Dec. 8, 2009 as U.S. Appl. No. 61/267,570.

Salanitro, J. P., et al., "Quantitative method for the gas chromatographic analysis of short-chain monocarboxylic and dicarboxylic acids in fermentation media," Applied Microbiology, Mar. 1975, pp. 374-381, vol. 29, No. 3, American Society for Microbiology.

Vázquez, M. J., et al., "Xylooligosaccharides: manufacture and applications," Trends in Food Science & Technology, 2000, pp. 387-393, vol. 11, Elsevier Science Ltd.

Foreign communication from a related counterpart application—International Preliminary Report on Patentability, PCT/US2010/046867, Feb. 28, 2012, 7 pages.

(56) References Cited

OTHER PUBLICATIONS

Foreign communication from a related counterpart application—International Search Report and Written Opinion, PCT/US2010/046867, Jun. 1, 2011, 11 pages.
Patent application entitled "Methods of making and using a ruminant gas reduction composition," by Matthew W. Lowe, et al., filed Feb. 24, 2012 as U.S. Appl. No. 13/392,288.
Foreign communication from a related counterpart application—European Examination Report, European Patent Application No. 09763380.4, May 23, 2012, 3 pages.
Foreign Communication from a related counterpart application—International Preliminary Report on Patentability, PCT/US2010/059528, Jun. 21, 2012, 8 pages.
De Castro, Fernando Basile, "The Use of Steam Treatment to Upgrade Lignocellulosic Materials for Animal Feed," Ph. D. Thesis, University of Aberdeen, Sep. 1994, 214 pages.
Office Action (Restriction Requirement) dated Apr. 8, 2013, 10 pages, U.S. Appl. No. 13/392,288, filed Feb. 24, 2012.
Office Action dated May 22, 2013, 24 pages, U.S. Appl. No. 13/392,288, filed Feb. 24, 2012.
De Castro FB. The use of steam treatment to upgrade lignocellulosic materials for animal feed. Ph.D. Thesis, University of Aberdeen. Sep. 1994.
Filing receipt and specification for provisional patent application entitled "Oligosaccharide Prebiotic Product Processed from Softwood Molasses," by Tom Lehtinen, et al., filed Jun. 9, 2008 as U.S. Appl. No. 61/059,960.
Filing receipt and specification for provisional patent application entitled "Natural Prebiotic Derived from Southern Yellow Pine Polysaccharides," by Tom Lehtinen, et al., filed Dec. 9, 2008 as U.S. Appl. No. 61/121,005.
Filing receipt and specification for provisional patent application entitled "Ruminant Gas Reduction Composition and Methods of Making and Using the Same," by Matthew W. Lowe, et al., filed Aug. 27, 2009 U.S. Appl. No. 61/237,396.
Filing receipt and specification for provisional patent application entitled "Nutritional Composition and Methods of Making and Using the Same," by Anne Chace Hopkins, et al., filed Dec. 8, 2009 as U.S. Appl. No. 61/267,570.
Foreign communication from a related counterpart application—United Kingdom Examination Report, Application No. GB1205330.2, May 1, 2013, 3 pages.
Office Action dated Sep. 25, 2014 (31 pages), U.S. Appl. No. 13/514,885, filed Jun. 8, 2012.
Willfor, Stefan, et al., "Spruce-derived mannans—A potential raw material for hydrocolloids and novel advanced natural materials," XP 002656400, Carbohydrate Polymers, 2008, vol. 72, pp. 197-210, Elsevier Ltd.
Moure, Andres, et al., "Advances in the manufacture, purification and applications of xylo-oligosaccharides as food additives and nutraceuticals," XP 002656401, Process Biochemistry, 2006. vol. 41, pp. 1913-1923, Elsevier Ltd.
Vazquez, M.J., et al., "Refining of autohydrolysis liquors for manufacturing xylo-oligosaccharides: evaluation of operational strategies," XP 025313229, Bioresource Technology, 2005, vol. 96, pp. 889-896, Elsevier, Ltd.
Vazquez, M.J., et al., "Enzymatic processing of crude xylo-oligomer solutions obtained by autohydrolysis of Eucalyptus wood," XP002656402, Food Biotechnology, abstract, 2002, p. 1.
Vazquez, M.J., et al., "Enhancing the potential of oligosaccharides from corncob autohydrolysis as prebiotic food ingredients," Industrial Crops and Products. 2006, vol. 24, pp. 152-159, Elsevier, Ltd.
Azumi, H., et al., "Xylo-oligosaccharide composition is useful as medicine with high regulation effect of intestinal condition and is not decomposed by digestive fluids," XP 002656403 and JP 2001 226409 A, WPI Thomson, abstract, Aug. 21, 2001, pp. 1-10.
Crawford, D.F., et al., "Evaluation of concentrated hemicellulose extract as cattle feed," XP 002580031, Journal of Animal Science. 1978, vol. 46, No. 1, pp. 32-40.
Foreign communication from a related counterpart application—Supplementary European Search Report, Application No. EP 09 76 3380, Aug. 23, 2011, 11 pages.
Foreign communication from a related counterpart application—International Search Report and Written Opinion, PCT/US2010/059528, Aug. 30, 2011, 12 pages.
Parajo, J.C., et al., "Production of xylooligo-saccharides by autohydrolysis of lignocellulosic materials," Trends in Food Science & Technology, 2004, vol. 15, pp. 115-120, Elsevier Ltd.
Office Action dated Jun. 25, 2015 (14 pages), U.S. Appl. No. 13/514,885, filed Jun. 8, 2012.
Office Action (Final) dated Feb. 18, 2015 (15 pages), U.S. Appl. No. 13/514,885, filed Jun. 8, 2012.
Kačuráková, M., et al., "FT-IR study of plant cell wall model compounds: pectic polysaccharides and hemicelluloses," Carbohydrate Polymers, 2000, pp. 195-203, vol. 43, Elsevier Science Ltd.
Office Action dated Oct. 16, 2015 (256 pages), U.S. Appl. No. 14/465,634, filed Aug. 21, 2014.
Office Action (Final) dated Nov. 6, 2015 (12 pages), U.S. Appl. No. 13/514,885, filed Jun. 8, 2012.

* cited by examiner

PREBIOTIC COMPOSITION AND METHODS OF MAKING AND USING THE SAME

CROSS-REFERENCE TO RELATED APPLICATIONS

This application claims priority to U.S. Provisional Application No. 61/059,960, filed on Jun. 9, 2008 and entitled "Oligosaccharide Prebiotic Product Processed from Softwood" and U.S. Provisional Application No. 61/121,005, filed on Dec. 9, 2008 and entitled "Natural Prebiotic Derived from Southern Yellow Pine Polysaccharides," each of which is incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Renewable biological source materials such as plants and wood comprise various biological polymers. For example, carbohydrates (or saccharides) are a major component of wood. Chemically, carbohydrates are simple organic compounds that are aldehydes or ketones with a plurality of hydroxyl groups, usually one on each carbon atom that is not part of the aldehyde or ketone functional group. Carbohydrates are comprised of repeating monomeric units termed monosaccharides which can link together to form polymers referred to as polysaccharides and oligosaccharides, which are present in hemicellulose recovered from renewable raw materials such as wood.

Carbohydrates that resist digestion in the small intestine but are fermentable in the large intestine have been shown to have added health benefits as prebiotics. As used herein, prebiotics refer to non-digestible food components that selectively stimulate the growth and/or activity of one or a limited number of beneficial bacteria in the colon, resulting in an improvement or maintenance of host health. An ongoing need exists for prebiotic compositions that may beneficially affect the health of the organism to which it is administered. Further it would be desirable to cost-effectively obtain prebiotics from a renewable resource such as wood.

SUMMARY

Disclosed herein is a prebiotic composition comprising soluble extractable material from a lignocellulosic source wherein the soluble extractable material comprises a hemicellulose. In an embodiment, the soluble extractable material comprises galactoglucomannans, xylans, arabinoxylans, or combinations thereof. In another embodiment the soluble extractable material comprises galactoglucomannans and the galactoglucomannans comprise glucose monosaccharide units, galactose monosaccharide units, and mannose monosaccharide units in a ratio of about 3 to about 1 to about 6. In an embodiment, the lignocellulosic source comprises the above and below-ground portion of a plant wherein the above-ground portion of a plant exhibits cambial growth. In another embodiment, the lignocellulosic source comprises a member of the family Pinaceae, a member of the family Fagaceae, a member of the order Saxifragales, or combinations thereof. In yet another embodiment, the lignocellulosic source comprises a member of the genus Pinus. In an embodiment a dietary fiber comprises the prebiotic composition. In another embodiment an admixture comprises the prebiotic composition and one or more pharmaceutical carriers.

Also disclosed herein is a method comprising administering the prebiotic composition to an organism for prophylactic treatment of a gastrointestinal ailment.

Also disclosed herein is a food product comprising the prebiotic composition.

Also disclosed herein is an admixture of the prebiotic composition with one or more feed products, feed liquids, feed supplements, or combinations thereof.

Also disclosed herein is a method of producing a composition, comprising providing a lignocellulosic source; extracting soluble materials from the lignocellulosic source to produce soluble extractable material; and processing the soluble extractable material to yield a prebiotic composition, wherein the prebiotic composition comprises hemicellulose and exhibits prebiotic activity. In an embodiment extracting soluble materials comprises softening the lignocellulosic source. In an embodiment softening of the lignocellulosic source comprises autohydrolysis, pulping, steam explosion, steam extrusion, or combinations thereof. In an embodiment the hemicellulose comprises monomers, oligosaccharides, and polysaccharides having a degree of polymerization from 1 to greater than about 500. In an embodiment the hemicellulose comprises xylans, arabinoxylans, galactoglucomannans, manans, derivatives thereof, or combinations thereof. In an embodiment the soluble extractable materials comprise monosaccharides, oligosaccharides, and polysaccharides composed of glucose, galactose, and mannose units in a ratio of about 3 to about 1 to about 6. In an embodiment, the method further comprises hydrolyzing the soluble extractable materials to produce a hydrolyzed composition. In an embodiment, the hydrolyzed composition comprises polysaccharides having a degree of polymerization of from about 2 to about 20. In an embodiment, the method further comprises dehydrating the soluble extractable materials.

Also disclosed herein is a method comprising administering the prebiotic composition to an organism having a gastrointestinal system. In an embodiment administration of the prebiotic composition improves the gastrointestinal health of the organism. In an embodiment administration of the prebiotic composition improves production of an organism-derived commodity, a biological function, or combinations thereof. In an embodiment the organism derived product or commodity comprise eggs, meat, milk, wool, or combinations thereof. In an embodiment the biological function comprises nutrient uptake, muscle growth, muscle development, weight gain, coat growth, survival, or combinations thereof. In an embodiment the prebiotic composition is administered as a food-additive.

DETAILED DESCRIPTION

Figure 1:
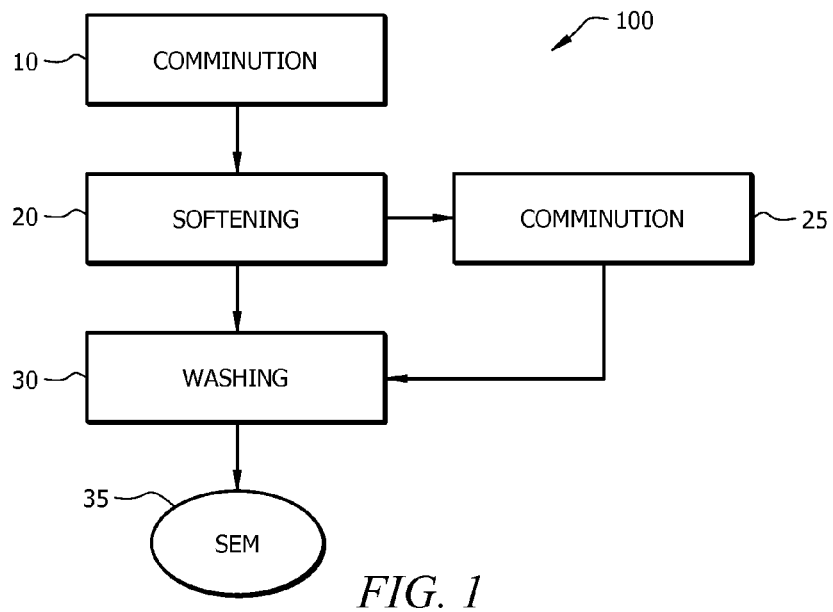
FIG. 1 is a flowchart of a method for isolating a prebiotic.

Although an illustrative implementation of one or more embodiments may be provided below, the disclosed systems and/or methods may be implemented using any number of techniques. This disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein is a prebiotic composition and methods of making and using same. In an embodiment, the prebiotic composition comprises soluble extractable materials from a lignocellulosic source. In an embodiment, the prebiotic composition is derived from a renewable, biological source material such as wood, bark, foliage, and roots. As is understood by those of skill in the art, wood refers to the organic material produced as secondary xylem in the stems of trees comprising various biological polymers including cellulose, hemicellulose, pectin, and lignin.

In an embodiment, the prebiotic is derived from a lignocellulosic source material. Herein the term "derived" refers to isolation of the material from an organism where it is present natively such that the material is no longer in contact with all components of its native milieu. In an embodiment, the prebiotic is derived from the above-ground portion of a plant source material. Nonlimiting examples of such plant source materials include rice, rice hulls, soybeans, cotton, corn, barley, sorghum, sugar cane, bamboo, canola, sunflower, maize, sesame, rapeseed, coconut, rye, lucerne, lentil, peas, soya, beans, safflower, *Poa* spp., *Panicum* spp., algae and byproducts or derivatives of production and processing of the aforementioned source materials. In embodiments wherein the plant source material is a member of the family Poaceae or Gramineae the prebiotic is not derived from the caryopsis. In an embodiment, the lignocellulosic source material does not comprise chicory root, larch trees, sugar beets, konjac, carob seed, cassia gum, locust bear gum, xanthan gum, wheat, oats, potatoes, guar gum or soy.

In another embodiment the prebiotic is derived from a lignocellulosic source material that exhibits cambial growth. For example, the source material may comprise a plant that is a member of the family Pinaceae, the family Fagaceae or the order Saxifragales. Alternatively the source material is derived from a member of the family Pinaceae. The family Pinaceae comprises coniferous trees commonly known as the pine family.

In embodiments, the source material comprises a material derived from a member of the genus *Pinus*. The genus *Pinus* comprises coniferous trees commonly known as the pines. In embodiments, the source material comprises a material derived from a member of at least one species collectively referred to as the Southern Yellow Pines (SYP). In embodiments, the source material comprises a material derived from a member of the species *Pinus taeda* L, and its hybrids commonly referred to as Loblolly Pine. In alternative embodiments, the source material comprises a material derived from a member of the species *Pinus elliotii* Englem, and its hybrids commonly referred to as the Slash Pine. In alternative embodiments, the source material comprises a material derived from a member of the species *Pinus echinata* Mill, and its hybrids commonly referred to as Shortleaf Pine. In alternative embodiments, the source material comprises a material derived from a member of the species *Pinus palustris* Mill, and its hybrids commonly referred to as the Longleaf Pines. Southern Yellow Pines of the type disclosed herein are native to the Southeast United States and may typically be found along the coastal plain from eastern Texas to southeast Virginia extending into northern and central Florida. These Southern Yellow Pines are also globally cultivated and as such it is contemplated other regions may also provide a source of such pines. Typically Southern Yellow Pines are characterized as having a height of 30-35 m (100-115 ft) and a diameter of 0.7 m (28") and may grow to 47 m (154 ft) with a diameter of 1.2 m (47"). Southern Yellow Pines may also be characterized by bark that is thick, reddish-brown, and scaly and leaves that are dark green, needle-like, and occur in bundles of up to three. The leaves are often twisted and have a length ranging from 20-45 cm (8-18").

In embodiments, a process of deriving a prebiotic from a source material (e.g., wood) comprises comminuting the source material, extracting soluble material from the source-material, and concentrating the extracted solubles. In an embodiment, a process of deriving a prebiotic from a source material (e.g., wood) comprises comminuting the wood, extracting oligosaccharides and polysaccharides (e.g., hemicellulose) from the source material via contact with a solvent (e.g., water), and concentrating the solvent extract. In an embodiment, a process 100 of deriving a prebiotic from a source material is shown in FIG. 1.

In an embodiment, the process 100 of deriving a prebiotic from a source material optionally comprises comminution of the source material at block 10 to reduce the physical size of the source material. For example, the wood source material may be chipped or comminuted prior to extracting the soluble material. As will be appreciated by those of skill in the art, comminuting the wood source material is an appropriate means of reducing the wood to a size that is both manageable and efficient for continued processing. Suitable machinery known to those of skill in the art may be employed to comminute the source material, non-limiting examples of which include tub grinders, wood chippers, chip-n-saws and the like. Further, the comminuted wood may be screened to ensure that the material is uniformly or substantially uniformly sized. In the following embodiments, it is presumed that the wood source material has been comminuted prior to further processing. Though one or more of the following embodiments may describe the performance of processes with respect to comminuted wood, it is specifically contemplated that comminution is not necessarily a prerequisite to these processes.

In an embodiment, the process 100 of deriving a prebiotic from a source material (e.g., wood) comprises extracting the soluble material from the wood. Any method known to one of ordinary skill in the art and not deleterious to the prebiotic may be employed to extract the soluble material from the wood. In an embodiment, the process of extracting the soluble material from the wood comprises softening the source material (e.g., wood) at block 20, optionally comminuting the softened wood at block 25, and contacting the softened wood with one or more solvents at block 30 into which the soluble material may partition. Herein "softening" refers to processes which decrease the structural integrity of the exposed cell walls of the source material.

In an embodiment, the source material (e.g., wood) is softened at block 20 using any methodology known to one of ordinary skill in the art and compatible with the components of the prebiotic composition. Nonlimiting examples of such methodologies include thermal, thermomechanical, thermochemical, mechanical, chemical, hydrothermal, acid hydrolysis, alkaline hydrolysis, organosolvent treatment, enzyme treatment, or combinations thereof. In an embodiment, the methodology comprises steam explosion and decompression wherein the source material is subjected to steam, pressure, and elevated temperature for some specified time period to soften and dissolve cell wall constituents.

In an embodiment, the source material is softened by a technique comprising autohydrolysis. As used herein, the term "autohydrolysis" refers to the process of subjecting the source material to a high temperature in the absence of chemicals but with moisture wherein organic acids are formed from functional groups such as acetyl groups liberated from the source material.

Specifically, the autohydrolysis process may comprise introducing the source material (e.g. comminuted wood) into a steam digester. In embodiments, the comminuted wood is steamed at a pressure ranging from 18-300 p.s.i., alternatively, from 50-250 p.s.i., alternatively, from 75-225 p.s.i. In embodiments, the comminuted wood will be allowed to remain in the steam digester for a period up to 10 minutes, alternatively, up to 15 minutes, alternatively, up to 20 minutes. In an embodiment, temperatures within the steam digester range from 212-420° F., alternatively, from 290-340° F., alternatively, from 295-335° F., alternatively, from 300-330° F. Not seeking to be bound by any particular theory, introduction into the steam digester softens the woods chips, thereby increasing the efficiency of later processing steps which seek to extract the soluble material.

In an embodiment, the source material is softened by a technique comprising pulping. Any pulping process known to one of ordinary skill in the art and not deleterious to the prebiotic may be employed to soften the source material. Examples of such processes are described in greater detail below.

In an embodiment, the source material (e.g., comminuted wood) is pulped using a mechanical pulping process. In these embodiments, the mechanical pulping process comprises separating the component wood fibers via the use of a plurality of grindstones, refining discs, knives, and like machinery known to those of skill in the art to mechanically disintegrate the comminuted wood, thereby reducing the comminuted wood to the fibrous components.

In an embodiment, the source material is pulped by subjecting the material to a pulping agent. In these embodiments, the pulping process comprises subjecting the comminuted wood to one or more chemicals and/or enzymes which will break down the lignin that holds the fibrous components together. Thus, as the lignin is degraded, the fibers of the wood are separated. Nonlimiting examples of chemical pulping processes include acid hydrolysis, alkaline hydrolysis, organosolvent treatment and the like.

In some embodiments other methodologies for softening the source material may be employed. Such methodologies may employ a variety of reaction parameters such as temperature, pressure, pH, varying reaction times and the like to extract the soluble material from the wood. For example, the source material may be softened by a steam extrusion process. Herein steam extrusion refers to a process wherein the source material (e.g., comminuted wood) is pressed through a die where compressed gases (e.g., steam) are developed and then expanded (released).

Hereinafter the source material whether subjected to a process of the type described herein (e.g., optional comminution followed by autohydrolysis or pulping) is termed the refined source material and for simplicity will hereinafter be referred to as the "refined wood." In an embodiment, refined wood is recovered from the process after block 25 of FIG. 1.

In some embodiments, the process 100 further comprises comminuting the refined wood at block 25. Communition and methods of carrying out same have been described previously herein and may likewise be used to reduce the size of the refined wood. The communited, refined wood may be passed from block 25 to block 30 for washing as described below.

Referring again to FIG. 1, the process 100 of deriving a prebiotic from a source material may further comprise washing the refined wood 30. The refined wood may be washed by contacting the material with a wash solution. The wash solution may comprise any material compatible with the components of the prebiotic. In an embodiment, the wash solution is an aqueous solution; alternatively the wash solution is water or consists essentially of water. Contacting of the refined wood and wash solution may be carried out using any suitable technique such as for example by showering the refined wood with a wash solution. As the refined wood is contacted with the wash solution the extractable compounds may be dissolved in or otherwise portioned into the wash solution which may then be collected. In an embodiment, the soluble material comprising oligosaccharides and polysaccharides (e.g., hemicellulose) present in the refined wood will be dissolved, suspended in, or otherwise partitioned into the wash solution.

In some embodiments, softening of the source material and extraction of the soluble material may be carried out concomitantly using a process such as solid-liquid countercurrent extraction. Herein solid-liquid countercurrent extraction refers to a process wherein a solid phase material (e.g., comminuted wood) and a liquid phase material (e.g., hot water) are contacted to each other by causing them to flow countercurrently to each other to adsorb part of the components contained in the liquid phase to the solid phase and simultaneously extract part of the components adsorbed to the solid phase into the liquid phase.

The wash solution obtained by the processes described herein comprises soluble material extractable from a source material of the type described previously herein. Hereinafter the wash solution obtained as described is termed the soluble extractable material (SEM), as recovered at block 35 of FIG. 1. In an embodiment, processes of the type described herein result in the extraction of greater than about 50% of the hemicellulose present in the source material, alternatively greater than about 60, 65, 70, 75, or 80% of the hemicellulose present in the source material.

In an embodiment, the SEM may be further processed by concentrating the solution to form a concentrated liquid. In embodiments, the SEM is concentrated to between 40 and 70% solids, alternatively to between 12% to 40% solids, alternatively to between 70% to 90% solids. The solids found in the SEM comprise approximately 93% carbohydrate material, approximately 4% ash, and less than approximately 1% each of protein, fat, or crude fiber and exhibit prebiotic activity.

In an embodiment, the SEM is dehydrated to remove excess moisture. The SEM may be dehydrated using any suitable dehydration process as known to those of skill in the art and compatible with the needs of the process (e.g., spray drying, drum drying). In an embodiment, the SEM may be dehydrated to a moisture content of less than about 18%, alternatively less than about 10%, alternatively less than about 5%. In an embodiment, the SEM is concentrated and/or dehydrated to yield a solids powder.

The SEM prepared as described herein may comprise monosaccharides, oligosaccharides and polysaccharides. The term oligosaccharide herein refers to a polymer comprising from about 2 to about 20 monosaccharide units while a polysaccharide herein refers to a polymer comprising greater than about 20 monosaccharide units. The number of monosaccharide units in a given oligosaccharide is termed the "degree of polymerization" (DP). For example, the SEM may comprise polysaccharides having a DP of greater than about 100, alternatively greater than about 150, 200, 250, 300, 350, 400, 450, or 500. In an embodiment, the SEM may comprise monomers, oligosaccharides, and polymers ranging from about 2 to about 500 DP as will be described in more detail later herein.

In embodiments the SEM comprises one or more oligosaccharides comprising a polysaccharide backbone; that is, the backbone comprises a plurality of glycosidically-linked monosaccharide units. In embodiments, the glycosidic linkage comprises a α-glycosidic link, a β-glycosidic link, or combinations thereof. In embodiments, the SEM comprises oligosaccharides comprising both α-glycosidic links and β-glycosidic links. In embodiments, the oligosaccharide will further comprise at least one side-chain. The side chain may comprise at least one monosaccharide unit glycosidically-linked to at least one saccharide unit of the polysaccharide backbone. Alternatively, the side chain may comprise at least one polysaccharide unit glycosidically-linked to at least one saccharide unit of the polysaccharide backbone.

In embodiments, the SEM comprises one or more oligosaccharides having monomeric units comprising an aldotriose monomer, an aldotetrose monomer, an aldopentose monomer, an aldohexose monomer, a ketotriose monomer, a ketotretrose monomer, a ketopentose monomer, a ketohexose monomer, a ribose monomer, an arabinose monomer, a xylose monomer, a lyxose monomer, an allose monomer, an altrose monomer, a glucose monomer, a mannose monomer, a gulose monomer, an idose monomer, a galactose monomer, a talose monomer, a ribulose monomer, a xylulose monomer, a psicose monomer, a fructose monomer, a sorbose monomer, a tagatose monomer, or combinations thereof.

In an embodiment, the SEM is further processed to reduce the DP of the constituent polymers. The DP of the SEM constituent polymers (e.g., polysaccharides) may be reduced by cleaving one or more of the glycosidic bonds between the monomer units of an oligosaccharide. Various methods can be used to cleave some of the glycosidic bonds between the monomer units while preserving the integrity of the sugar units. For example, the glycosidic bonds may be hydrolyzed. Hydrolysis of the glycosidic bonds can be achieved through any mechanism known to one of ordinary skill in the art and compatible with the needs of the process. For example hydrolysis of the glycosidic bonds may be carried out employing chemical, enzymatic, thermal, or ultrasonic processes. Process variables such as reagent concentration, pH, temperature, time, and reactant can determine the degree of hydrolysis. Thus, one of ordinary skill in the art with the benefits of this disclosure may select hydrolysis reaction conditions suitable for the production of specific polymer chain lengths.

In embodiments, the DP of the SEM constituent polymers is reduced by acid hydrolysis of the material. For example, an acid for cleaving glycosidic bonds suitably comprises a weak acid. Non-limiting examples of such a weak acid include triflouroacetic acid (TFA), acetic acid, and oxalic acid. Alternatively, in embodiments, an acid for cleaving glycosidic bonds suitably comprises a strong mineral acid. Non-limiting examples of such a strong mineral acid include sulfuric acid and hydrochloric acid. In various embodiments, numerous combinations of exposure time, temperature, and acid concentration can be used to hydrolyze any large DP hemicellulose polysaccharides to the DP ranges disclosed herein.

In alternative embodiments, the DP of the SEM constituent polymers is reduced enzymatically. For example, enzymes may be employed to cleave the polymer chains at specific linkages. Numerous enzymes, including but not limited to β-mannanase and glucosidases, are suitable for use. Such enzymes and reaction conditions suitable for enzymatic cleavage of the SEM would be known to one of ordinary skill in the art with the aid and benefits of this disclosure.

Hydrolysis of the SEM as described herein produces a material hereinafter termed the "hydrolyzed hemicellulose material (HHM)." The HHM may have a DP of about 2 to about 30, alternatively about 2 to about 20, alternatively about 2 to about 15, alternatively about 2 to about 12. In an embodiment, the HHM comprises oligosaccharides having from about 3 to about 5 DP, alternatively from about 9 to about 14 DP, alternatively from about 16 to about 18 DP.

In an embodiment, the HHM or the SEM is further processed by contacting the material with a precipitating agent. Upon contact with a precipitating agent, HHM/SEM-derived oligosaccharide fractions having prebiotic functionality of the type described herein may be precipitated from the solution. In embodiments, a material containing prebiotic activity is precipitated from the HHM or SEM when the HHM or SEM is contacted with a precipitating agent comprising an alcohol. Alternatively, a material containing prebiotic activity is precipitated from the HHM or SEM when the HHM or SEM is contacted with ethanol. Further processing of the mixture comprising the precipitant may include removing the precipitating agent (e.g., ethanol) using any suitable technique (e.g., evaporation). The resulting precipitated material, hereinafter termed the precipitate prebiotic (PP), may be dried or resuspended in an appropriate solvent.

Additional processing of the PP may involve subjecting the material to enrichment methods in order to concentrate fractions having a specific DP or remove non-active (e.g., non-prebiotic) compounds. In embodiments, the PP is further enriched by subjecting the previously described SEM and/or its derivatives (e.g., HHM) to additional separation procedures. In these embodiments, such separation procedures include but are not limited to chromatographic separation, ion exchange separation, filtration, microfiltration, ultra filtration, or the like. Such a separation process may be employed to remove any remaining non-desirable materials (e.g., monosaccharide, lignin, salts, phenolics, ash, etc.) from the product composition. Additionally compounds, such as phenolics or lignin, may be removed at various points during processing.

In an embodiment, the SEM, HHM, and/or PP comprise hemiceullulose comprising xylans, arabinoxylans, galactoglucomannans, or combinations or derivatives thereof. In an embodiment, the SEM, HHM, and/or PP comprise xylans. In some embodiments, the xylan is comprised of a backbone chain of xylose units which are linked by β-(1,4)-glycosideic bonds and branched by α-(1,2)-glycosidic bonds with 4-O-methylglucoronic acid groups. In some embodiments, O-acetyl groups replace the OH groups in the C2 and C3 groups. A partial structure of a xylan is shown in Structure 1.

Structure 1

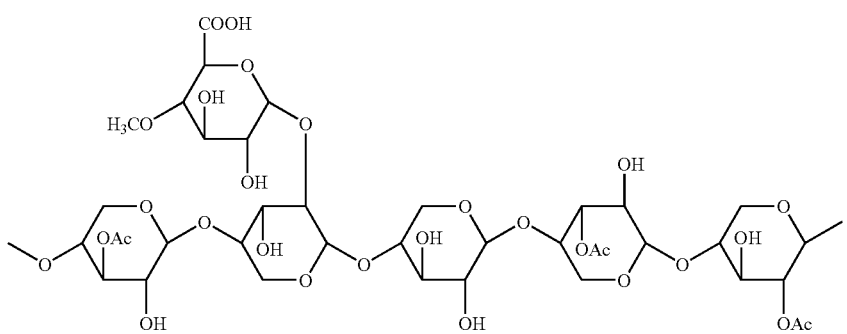

In an embodiment the SEM, HHM, and/or PP comprise an arabinoxylan. Arabinoxylans consist of α-L-arabinofuranose residues attached as branch-points to β-(1→4)-linked D-xylopyranose polymeric backbone chains. These may be C2 or C3-substituted or C2 and C3-di-substituted. The arabinose residues may also be linked to other groups attached such as glucuronic acid residues, ferulic acid crosslinks and acetyl groups. The most stable conformations comprise α-L-arabinofuranose and β(1→4)-linked D-xylopyranose residues. The furanose can, however, take up a number of other conformations with similar energy whereas the chair conformation of the pyranose residue is fixed. Arabinoxylans may comprise greater than about 500 monosaccharide repeating units, alternatively greater than about 1000 monosaccharide repeating units, alternatively from about 1500 to about 5000 monosaccharide repeating units. A partial structure of an arabinoxylan is shown in Structure 2.

Structure 2

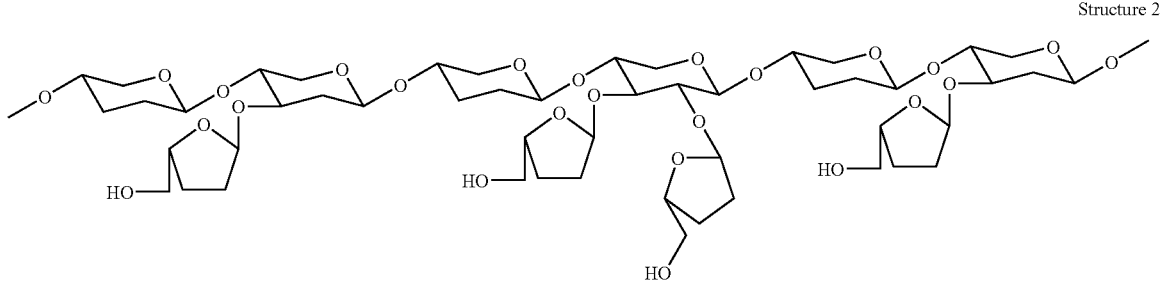

In embodiments, the SEM, HHM, and/or PP comprise an oligosaccharide comprising monomeric units having glucose monomers, galactose monomers, and mannose monomers in the form of a galactoglucomannan (GGM). In embodiments, the GGM comprises a backbone of β-1-4 linked mannose units with randomly spaced glucose units included and occasional α-1-6 galactose unit side chains. In embodiments, the hydroxyl groups of one or more monomeric units comprising the GGM backbone are partially substituted with O-acetyl groups at C-2 and C-3 positions. A non-limiting representative GGM structure is shown in Structure 3:

Structure 3

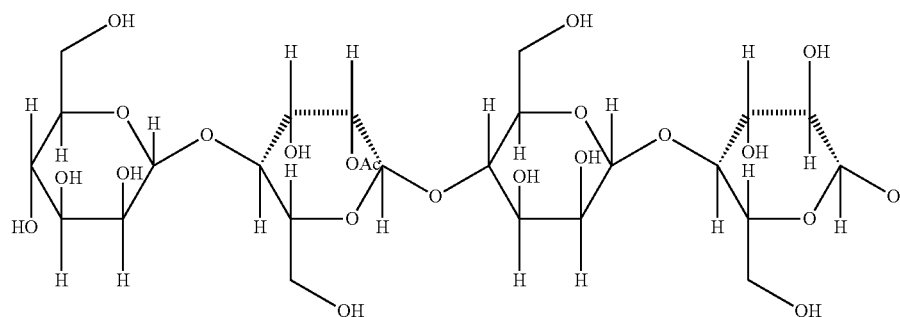

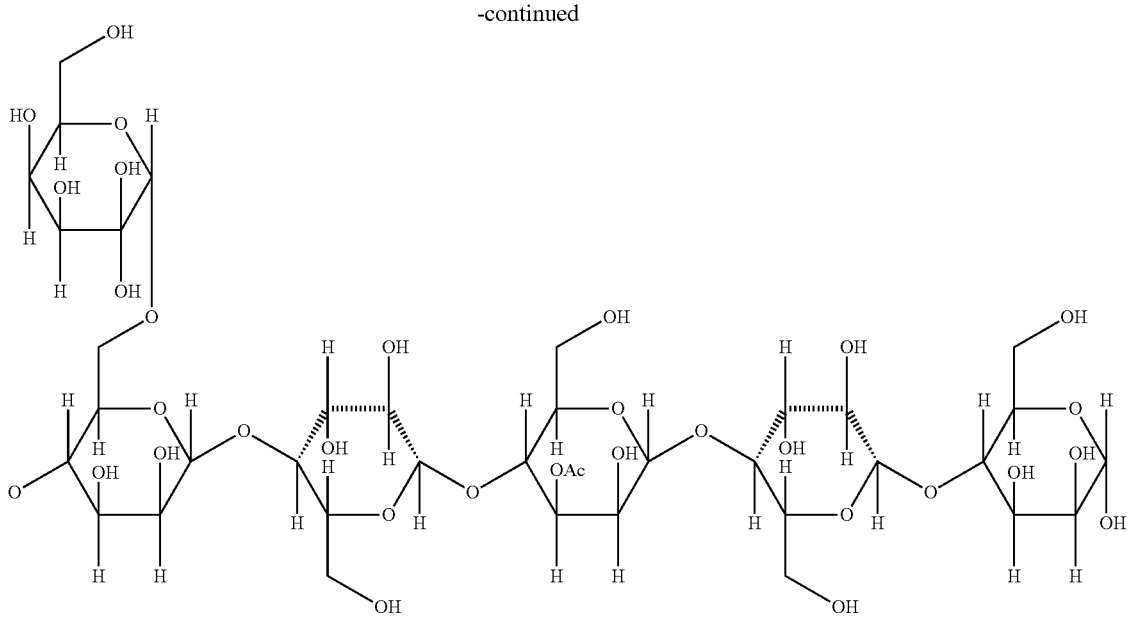

In an embodiment, the GGM oligosaccharide comprises glucose, galactose, and mannose in a ratio of 3 to 1 to 6 respectively.

As will be understood by one of ordinary skill in the art, variations in the methodology for obtaining the SEM, HHM, and/or PP may result in variations in the amounts and/or nature of the components of the SEM, HHM, and/or PP.

For simplicity hereinafter the disclosure will refer to a prebiotic composition (PRE-COMP). It is to be understood said PRE-COMP is obtained from a source material of the type described herein using the methodologies described herein. The PRE-COMP may comprise the SEM, HHM, PP, components or fractions thereof (e.g., fractions having a given DP), derivatives thereof, or combinations thereof, of the type described herein.

In an embodiment, the PRE-COMP comprise hemiceullulose comprising xylans, arabinoxylans, GGMs or combinations thereof. In an embodiment, the PRE-COMP comprises the SEM, HHM, PP, or a SEM-derived fraction. In an embodiment, the PRE-COMP comprises a HHM having DP of from about 2 to about 20. In an embodiment the PRE-COMP comprises a GGM having a galactose:glucose:mannose ratio of about 3:1:6.

As discussed previously herein, prebiotics refer to nondigestible food components that selectively stimulate the growth and/or activity of one or a limited number of beneficial bacteria in the colon, resulting in an improvement or maintenance of host health. The term "gut flora" and "microflora" refer to microorganisms that normally live in the digestive tract of a human or animal. The human gut flora comprises pathogenic, benign, and beneficial microbial genera. For example, the gut flora of a normal, healthy animal may comprise beneficial bacteria such as lactobacilli, bifidobacteria, and non beneficial gut bacteria include bacteroides, coliforms, clostridia, and sulfate-reducing bacteria. A predominance of the latter can lead to intestinal disorders, acute or chronic, including gastroenteritis, inflammatory bowel syndrome, irritable bowel syndrome, and some intestinal cancers.

The PRE-COMP may beneficially affect the host by selectively stimulating the growth and/or the activity of one or more of the beneficial bacteria in the colon, thereby resulting in an improvement in the health of the host. For example, a mammal being administered a PRE-COMP may experience the benefits of maintaining gastrointestinal health, reducing cholesterol, attenuating blood dextrose, improving mineral absorption, or combinations thereof.

In an embodiment, an effective amount of the PRE-COMP may be administered to an organism and function as a prebiotic to confer beneficial health effects. Such beneficial health effects may include digestive resistance, lower gut fermentation, selective promotion of beneficial microflora (e.g., lactobacilli and/or bifidobacteria) and reduction of pathogenic or nonbeneficial microflora (e.g., bacteroides, coliforms, clostridia, and/or sulfate-reducing bacteria). Without wishing to be limited by theory, PRE-COMPs of the type described herein may confer beneficial health effects by any number of mechanisms nonlimiting examples of which include competitive exclusion and/or pathogen binding and/or site colonization interference, production of short chain fatty acids and/or decrease in pH in the gastrointestinal (GI) tract of the organism to which it is introduced.

In an embodiment, a PRE-COMP may be administered to an organism in order to confer beneficial health effects of the type described herein. Alternatively, the PRE-COMP may be administered to an organism experiencing or anticipated to experience one or more adverse health events for which a prebiotic would ameliorate, mitigate, or prevent said adverse health event. For example, a PRE-COMP may be administered to an organism experiencing an adverse health event involving alterations in the gut flora. Alternatively, a PRE-COMP may be administered to an organism having an expectation of developing an adverse health event involving alterations in the gut flora. For example, an organism having been administered a pharmaceutical compositions (e.g., an antibiotic) may have an increased probability of developing one or more symptoms of gastrointestinal distress (e.g., diarrhea) associated with the use of the antibiotic. In an embodiment, an effective amount of a PRE-COMP may be coadminstered with the pharmaceutical composition. Alternatively an effective amount of a PRE-COMP may be administered prior to and/or subsequent to administration of the pharmaceutical composition. In either embodiment, the administration of a PRE-COMP may mitigate or prevent the development of gastrointestinal distress associated with the use of the pharmaceutical composition.

In an embodiment, this disclosure provides for compositions comprising a PRE-COMP and a pharmaceutically acceptable carrier. The term "composition" is intended to encompass a product comprising the active ingredient(s) (e.g., PRE-COMP), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present disclosure encompass any composition made by admixing a PRE-COMP, additional active ingredient(s), and pharmaceutically acceptable excipients.

The term "effective amount" as used herein means that amount of the PRE-COMP that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. It is contemplated that the compositions of the present disclosure may also be introduced to an organism in amounts less than a predetermined therapeutically and/or prophylatically effective amount. For example, a sub-effective amount of the disclosed compositions may be administered as an admixture of the composition with one or more food products and may serve to alter various properties of the food product (e.g., texture, appearance, taste, etc.).

Any suitable route of administration may be employed for providing an organism (e.g., human or animal) a PRE-COMP. Dosage forms include tablets, troches, dispersions, suspensions, solutions, capsules and the like. The most suitable route in any given case will depend on the nature and severity of the conditions being treated and on the nature of the active ingredient. They may be conveniently presented in unit dosage form and prepared by any of the methods well-known in the art of pharmacy.

In practical use, a PRE-COMP can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers may be employed. If desired, tablets may be coated by standard aqueous or nonaqueous techniques.

Pharmaceutical compositions comprising a PRE-COMP suitable for oral administration may be presented as discrete units such as capsules, cachets or tablets each containing a predetermined amount of the active ingredient (e.g., PRE-COMP), as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

PRE-COMPs may be used in combination with other drugs that are used in the treatment/prevention/suppression or amelioration of the adverse health events for which PRE-COMPs of the type described herein are useful.

In an embodiment, the PRE-COMP is administered to an organism having a GI tract. Administration of the PRE-COMP may comprise preparing the PRE-COMP in a suitable orally ingestible form and providing the suitable orally ingestible form to the organism. Suitable orally ingestible forms are discussed herein in further detail, although other suitable ingestible forms and methods of formulating same will be appreciable by those of skill in the art with the aid of this disclosure.

In an embodiment, a suitable orally ingestible form comprises a PRE-COMP incorporated within a food, feed, or fodder product. The PRE-COMP may be incorporated within the food, feed, or fodder product as a dry powder or a liquid. Nonlimiting examples of food, feed, or fodder products into which the PRE-COMP may be incorporated include compound feeds and premixes such as pellets, nuts, nuggets, oil cakes, press cakes, various meals (e.g., fishmeal), or combinations thereof. Such food, feed, or fodder product may be prepared by admixing or blending the PRE-COMP with a suitable carrier or diluent. Nonlimiting examples of suitable carriers may include grass and other forage plants, plant oils, seeds, grains, crop residues, sprouted grains, legumes, alfalfa meal, soybean meal, cottonseed oil meal, linseed oil meal, sodium chloride, cornmeal, molasses, urea, corncob meal, rice kernel, and the like. The carrier promotes a uniform distribution of the active ingredients in the finished feed into which the carrier is blended. It thus may ensure proper distribution of the active ingredient throughout the food, feed, or fodder product.

In an embodiment, a suitable orally ingestible form comprises a PRE-COMP prepared as a nutritional supplement. Such a nutritional supplement may be ingestible by an organism alone or with another food, feed, fodder, forage product, snack, treat, or enjoyment product. In various embodiments, nutritional supplements may be prepared in a wet, semi-wet, or dry form. Nonlimiting examples of suitable nutritional supplement forms include powders, granules, syrups, and pills; other suitable forms will be known to those of skill in the art with the aid of this disclosure. In an embodiment, a nutritional supplement may be added to another food, feed, fodder, or forage product. For example the nutritional supplement may comprise a powder or syrup which is dispensed with (e.g., poured onto) hay, pellets, forage, or the like. Alternatively, in an embodiment a nutritional supplement is provided without any other food or nutrient. For example, the nutritional supplement may comprise a syrup or gel which may be licked by an organism (e.g., from a tub or other suitable dispenser) or water-soluble powder dissolved in water provided for ingestion by the organism. Other suitable means of dispensing a nutritional supplement will be appreciated by those of skill in the art viewing this disclosure.

As will be appreciated by those of skill in the art, the ingestible forms may be formulated for ingestion by one or more organisms, nonlimiting examples of which include livestock such as cattle, swine, horses, sheep, goats, poultry, fish, domesticated companionship species such as dogs, cats, fish, and rodents or undomesticated wildlife such as deer, moose, elk, migratory and non-migratory fowl, decapods, and fish.

In an embodiment administration of a PRE-COMP improves the overall health of the organism to which it is administered. In some embodiments, the overall improved health of the organism may be evidenced by an increase in biological functions such as nutrient uptake, muscle growth, muscle development, weight gain, coat growth, survival, or combinations thereof. In another embodiment administration of the PRE-COMP to an organism results in an increased yield in an organism derived commodity such as eggs, meat, milk, wool, or combinations thereof.

EXAMPLES

The embodiments having been generally described, the following examples are given as particular embodiments of the disclosure and to demonstrate the practice and advantages thereof. It is to be understood that the examples are presented herein as a means of illustration and are not intended to limit the specification of the claims in any manner.

Example 1

In Vitro Digestion and Fermentation of Oligosaccharide Composition, as Compared to Controls As discussed with respect to the aforementioned embodiments, it is desirable that a prebiotic compound resist digestion in the upper gastrointestinal (GI) tract so that it will pass intact into the large intestine where it will then be fermented by beneficial gut bacteria.

In this example, two sets of experiments were performed on a PRE-COMP derived from Southern Yellow Pine species via the processes described in one or more of the foregoing embodiments. The chemical and in vitro digestion and fermentation characteristics of PRE-COMP, PRE-COMP derived material, and a control prebiotic material were investigated. These experiments indicated that the chemical composition, as well as the digestibility and fermentative properties, of SEM and SEM derived materials displayed prebiotic activity. The following samples were tested:

| No. | SAMPLE | SOURCE | PROCESSING |
|---|---|---|---|
| 1 | Soluble Extractable Materials (SEM) | Soluble Extractable Materials | As produced according to conditions mentioned herein |
| 2 | PP | SEM-HHM | Mild acid hydrolyzed SEM, partially purified with ethanol precipitation, dried. |
| 3 | PP-DP fractions | Precipitate prebiotic | Purified glucogalactomannose oligosaccharide fractions separated by size-large DP 9-14, medium DP 6-8, small DP 3-5 |
| 4 | scFOS | beet or cane sugar | Commercially available prebiotic oligosaccharide-included in study as a prebiotic control |
| 5 | YCW product | yeast | Relatively crude preparation from inactivated yeast cells-included as a mannan control |

The PP sample is an enriched SEM fraction prepared by mild acid hydrolysis with 0.2M TFA, ethanol precipitation, centrifugation, and lyophilization. The three PP-DP fractions used in the experiment were prepared by passing the PP material through a size exclusion column to attain varying degrees of polymerization: 3-5 DP, 6-8 DP, and 9-14 DP.

Figure 2:
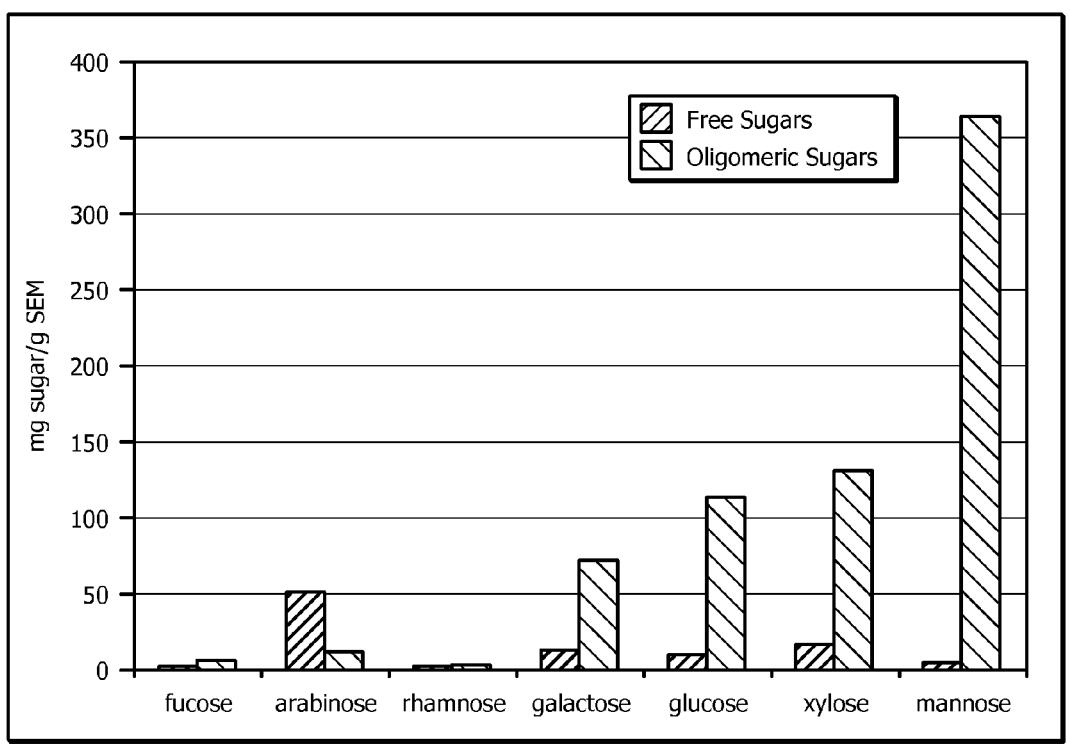
FIG. 2 is a graph illustrating total sugar composition for the samples from Example 1.

The scFOS sample is short chain fructooligosaccharide, a known, commercially available, prebiotic. It is generally produced from sucrose by an enzymatic or fermentation process, and probably has a DP of 3-4. YCW product is an inactivated yeast product that is sold for use as a food additive with poultry, young livestock, and aquaculture feed and commercially available. In this example, the free sugars were first extracted from SEM-Sample 1 and analyzed using high pressure liquid chromatography (HPLC)/Ion Chromatography. Sample 1 was then subjected to complete depolymerization with sulfuric acid and the sugar content was again determined using HPLC/Ion Chromatography. The difference between the free sugars and the total sugars indicates the amount of oligomeric or polymeric sugars. FIG. 2 shows the amounts of free and oligomeric sugars present in the SEM, Sample 1, measured in mg of sugar per gram of Sample 1(dry matter basis). This shows that galactose, glucose, xylose, and mannose are all present mainly in oligomeric form. In these experiments, the compositional analysis of the samples tested indicated that all of the samples contained >90% organic matter, with the exception of the PP sample, Sample 3, contained about 13% ash. This is likely due to the concentration of salts and ionic matter in the processing of SEM into PP.

The free sugars in several saccharide preparations were determined. These included SEM, PP, scFOS, YCW product, and three PP-DP fractions. The composition of YCW product is reported to be 22-24% mannans with about 16% protein, 25% β-glucans, 4% ash, and 20% fat. The amount of free sugars found in various saccharide preparations was determined. Samples 1 and 2 are similar in the quantity and type of free sugars found. The PP, Sample 3, is also similar to that of the whole SEM, Sample 1, with the notable exception that it contains a higher level of free mannose than the SEM. This likely caused by the hydrolysis procedure and the relatively crude separation step which was used. The scFOS and the YCW product samples, Samples 4 and 5 respectively, have low free monosaccharide levels, except some sucrose in the scFOS, and the large, medium, and small PP-DP fractions had no free sugar content.

Figure 3:
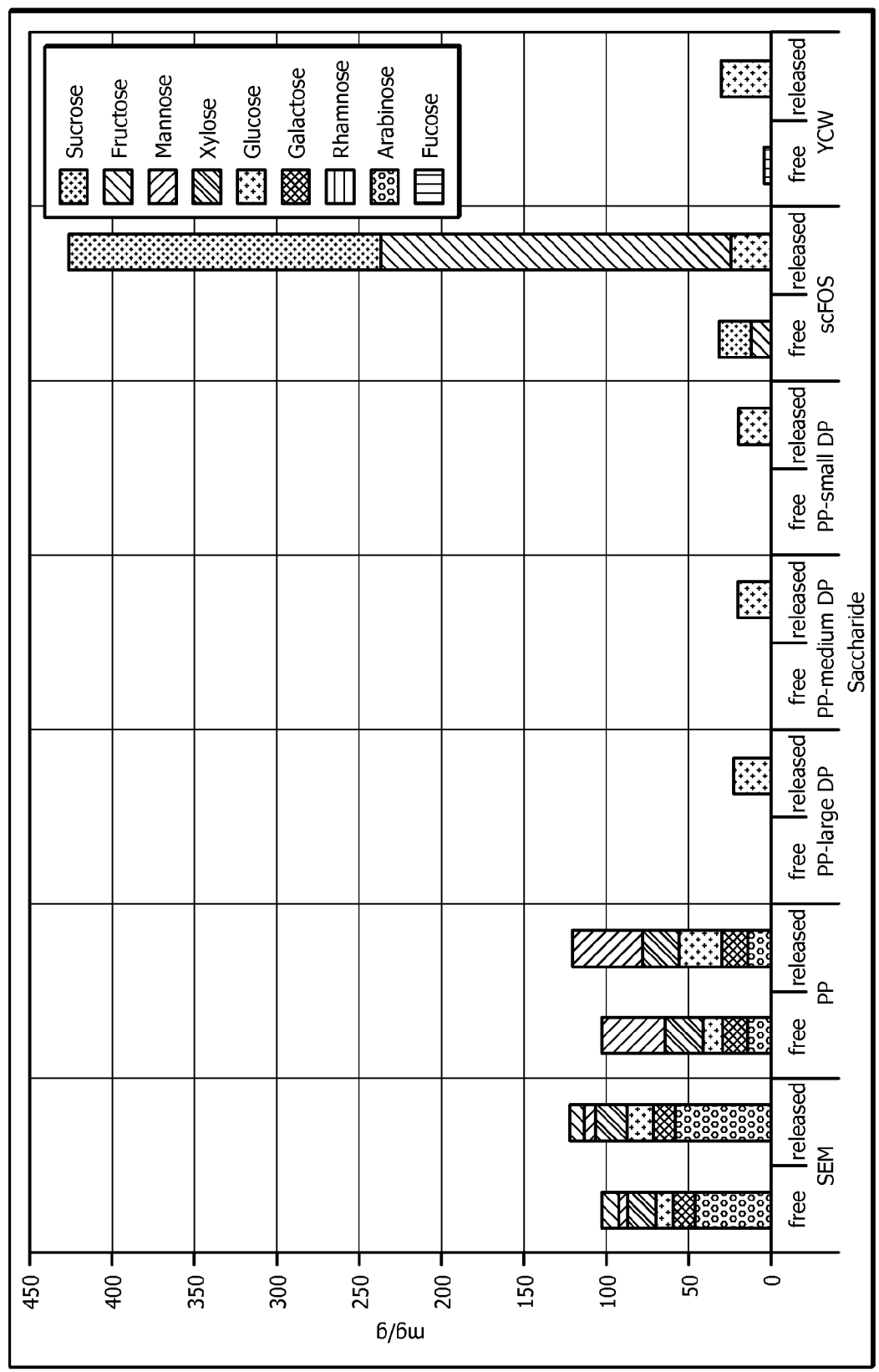
FIG. 3 is a graph illustrating the free sugars and released sugars during simulated digestion conditions.

The gastric and small intestine in vitro simulated digestion experiments performed in this example involve treating the samples for 6 hours with HCl-pepsin and 18 hours with pancreatin, and then measuring the released monosaccharides. For an oligosaccharide to exhibit prebiotic functionality, it must survive digestion nearly intact in order to move into the large intestine for fermentation. Therefore, high levels of released sugars indicate hydrolysis of the glycosidic bond between monomers as a result of the digestion conditions. FIG. 3 demonstrates the relative amounts of free sugars and the corresponding amounts of released sugars (corrected for free sugars). SEM and PP samples (Samples 1 and 3 respectively) show that the released sugars are very close in concentration to the quantities of free sugars present in the SEM, indicating near complete digestion of free sugars and little release of sugars from the hydrolyzed oligosaccharides. The YCW product, large, medium, and small PP-DP fractions samples had little free or released sugars. The scFOS sample had a high hydrolytic digestibility coefficient with a large amount of sucrose and fructose released and the oligosaccharide was broken down under digestion conditions.

As discussed above, a prebiotic oligosaccharide must support fermentation within the large intestine. This experiment simulated large bowel fermentation of the residue of saccharide left after gastric-small intestine digestion. This is done in the presence of microbiota from canine fecal material for a time of 12 hours, the residence time in the large intestine for non-ruminants. Carbohydrates in the colon are fermented to short chain fatty acids (SCFA), principally acetate, propionate and butyrate. SCFA are rapidly absorbed by the colonic mucosa and supply energy to the host and contribute substrates to several important metabolic pathways. Protein reaching the colon is fermented to branched chain fatty acids.

Figure 4:
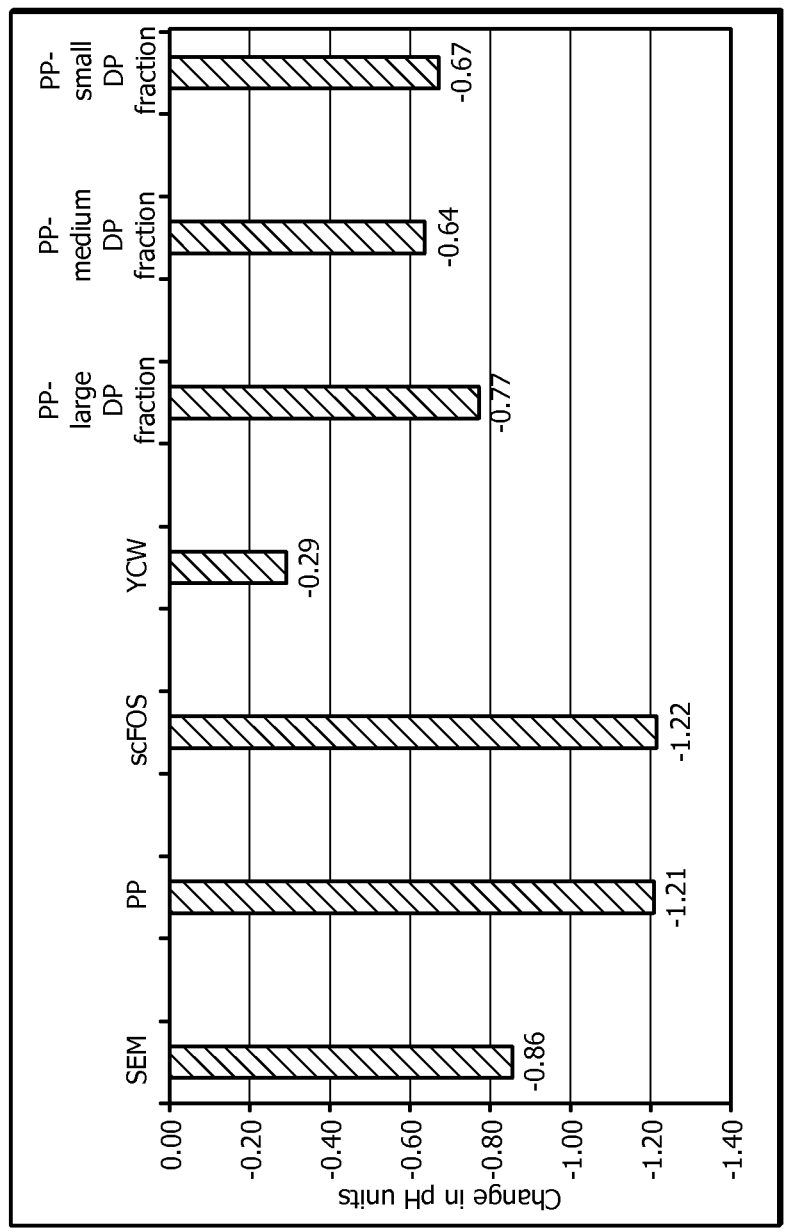
FIG. 4 is a graph illustrating the pH change during fermentation.

The production of SCFA is indicated by a drop in the pH of the fermentation media. FIG. 4 shows the drop in pH in fermentation media containing the different saccharide samples. All samples tested, with the exception of YCW product, showed an appreciable drop in pH.

Figure 5:
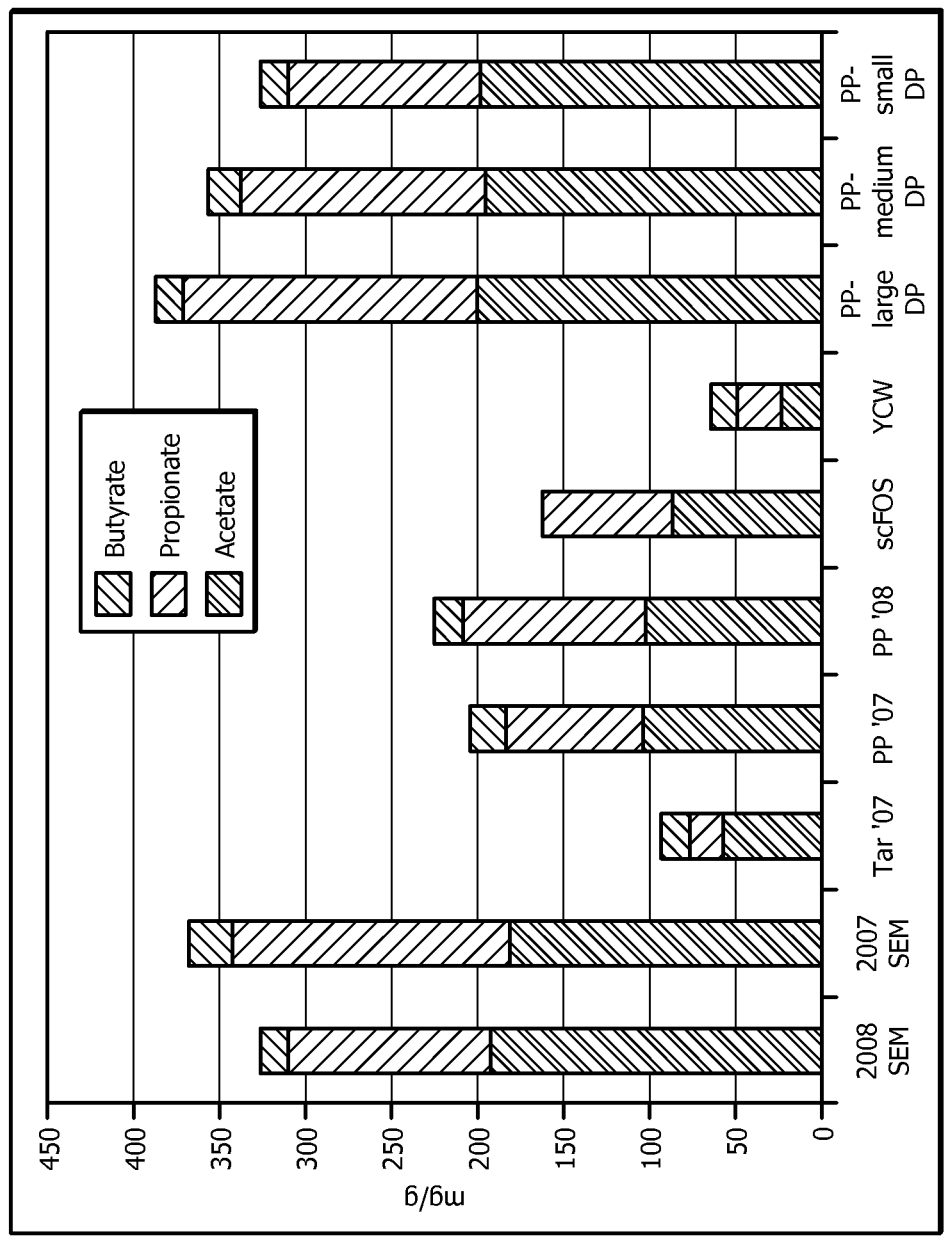
FIG. 5 is a graph illustrating short-chain fatty acid production.

The SCFA production during the simulated large bowel production is shown in FIG. 5. Included in this figure is data involving PP and the corresponding SEM "tar." The tar was the residue remaining after the PP has been processed from the SEM. It is believed that this fraction contains phenolics and other miscellaneous materials. The two SEM samples and all three of the PP-DP fractions were very well fermented as evidenced by the abundant SCFA production. The scFOS was only moderately fermented, likely due to the fact that a great portion of this sample was hydrolytically digested in the first, simulated digestion stage of the experiment. The YCW product was poorly fermented, with little SCFA production, as was the tar residue. The PP sample was moderately fermented, with similar results from the both samples.

Figure 6:
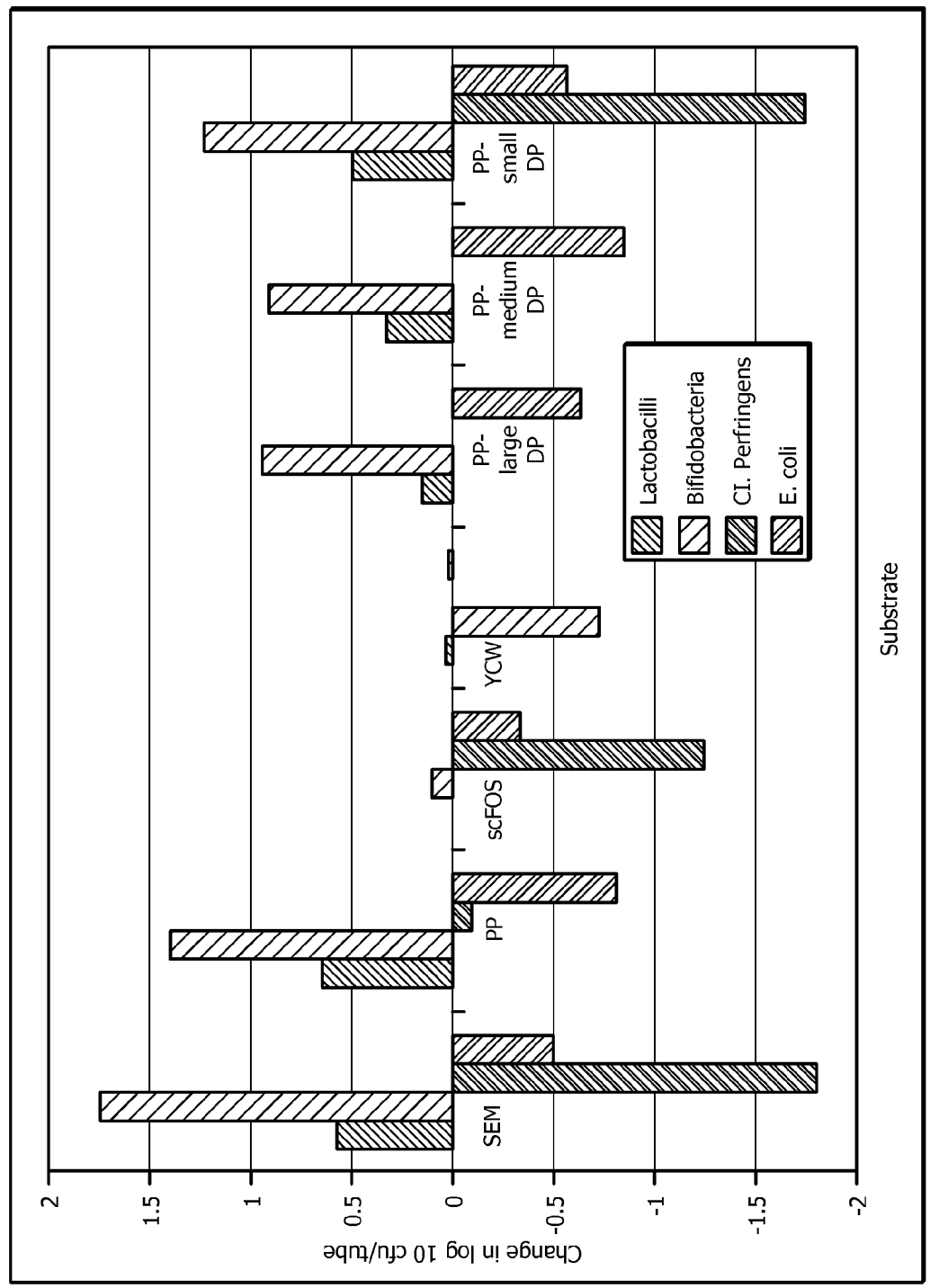
FIG. 6 is a graph illustrating change in microflora during fermentation.

In addition to resisting digestion and supporting fermentation, a substance must also selectively stimulate the growth and/or activity of beneficial intestinal bacteria to be classified as a prebiotic. The prebiotic effect can be determined by fermenting fecal suspensions with substrates and assessing growth through molecular based microbiological techniques. In a study the SEM, Sample 1, and SEM derived fractions, Samples 2 and 3, as well as control materials were subjected to in vitro gastric and small intestine digestion as described above. That material was then used in a model that simulated large bowel fermentation. Microbial populations were measured by DNA extraction from fermented samples, followed by quantitative polymerase chain reaction (qPCR). Quantitative PCR was performed for bifidobacteria, lactobacilli, *E. coli*, and *C. perfringens* at 0 hours and 12 hours of fermentation, with appropriate controls. The bifidobacteria and lactobacilli are bacterial geneses of beneficial gut bacteria. The *E. coli* and *C. perfringens* are pathogenic bacteria. The results are shown in FIG. 6.

All preparations of SEM (including SEM, PP, large, medium, and small PP-DP fractions) supported the growth of the beneficial bacteria lactobacilli and bifidobacteria. The effects of the SEM-based material were far greater than with the controls of the short chain fructooligosaccharide (scFOS) or YCW, which are both commercially available materials. The SEM based materials also show deleterious effects on the pathogenic bacteria.

Thus, the SEM derived material has been demonstrated to fulfill the criteria of a prebiotic by resisting digestion, being fermented by intestinal microflora, and selectively stimulating the growth of health-promoting intestinal bacteria.

Figure 7:
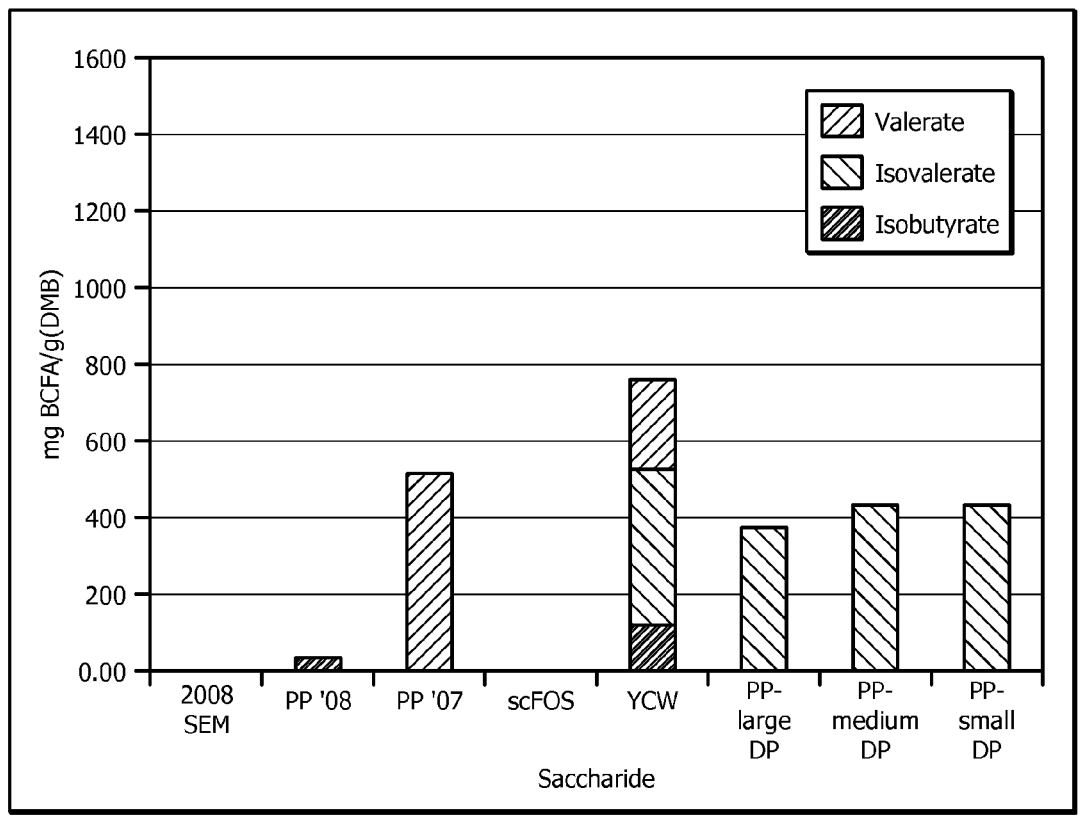
FIG. 7 is a graph illustrating the branched chain fatty acids produced during fermentation.

The production of branched chain fatty acids (BCFA) during simulated large bowel fermentation was determined (see FIG. 7). The production was low for all samples but was greatest for YCW product and PP-DP fractions. It is believed that BCFAs are a product of protein fermentation, and there is no protein in the PP-DP fractions. Without wishing to be limited by theory, these results could imply that these fractions are binding to microbes that contain protein; in that binding to gut microbiota is a suggested mechanism for mannan function.

Example 2

Growth Rates and the Susceptibility to Pathogenic Bacteria as Compared to Controls In this example, a two-phased hybrid striped bass feeding trial was conducted to evaluate a prebiotic material derived from a Southern Yellow Pine species denoted "SEM" via one or more of the foregoing methods at different inclusion rates in the diet of juvenile hybrid striped bass, to assess growth performance (weight gain) and feed efficiency of the fish over an 8-week feeding period, and to evaluate the effectiveness of the prebiotic material to convey disease resistance after controlled exposure to *Streptococcus iniae*. *Streptococcus iniae* is a gram positive bacteria responsible for causing high losses in farmed marine and freshwater finfish in warmer regions.

Phase 1 included an 8-week feed efficiency and weight gain performance trial of diets containing the prebiotic at 0.5%, 1%, and 1.5% inclusion rates. A basal diet and a commercial yeast-based product treatment were also included. Phase 2 included a 7-day bacterial (*Streptococcus iniae*) challenge period on a subset of the original fish to assess potential effects of the prebiotic-supplemented diets on disease resistance. Following the 8-week feeding trial, all diets containing the prebiotic exhibited numerically higher percent weight gain compared to the basal diet and yeast product. Contrast analysis following ANOVA indicated that the diet with 1% of an SEM of the type described herein increased tank weight gain significantly as compared to the basal diet ($p=0.0562$) and the diet with 1% yeast-based material ($p=0.0523$). At the 1% and 1.5% inclusion rates of an SEM of the type described herein, feed efficiency was also numerically higher and survival was significantly improved ($p=0.0255$) over the basal diet at the end of the feeding period. Following the 7-day *Streptococcus* challenge, fish fed a diet containing 1.5% of an SEM of the type described herein exhibited significantly higher ($p=0.0611$) survival than fish on all other treatments including the basal and yeast-based diets. These results indicate that an SEM of the type described herein can improve weight gain, feed efficiency, and increase survival of fishes.

In this example, test diets were prepared by supplementing the basal diet (negative control) with graded levels of an SEM of the type described herein (SEM) at 0.5, 1.0, and 1.5% of the diet in place of cellulose (dry weight basis). A positive control consisted of the basal diet supplemented with a commercially available yeast cell wall (YCW) product at 1% dry weight. Diets were formulated to contain 40% crude protein, 10% lipid, and 3.4 kcal estimated digestible energy/g. The fish were stocked 15 fish to a tank with four replicate tanks per treatment. Tanks were 110L aquaria linked to a recirculating water system, maintained indoors. Total fish weight per tank (g) and mortality (counts) were measured weekly during the 8-week feeding period. To address disease resistance following the feeding portion of the study, replicated subsamples of fish representing each diet were inoculated with *Streptococcus iniae*, (strain isolate source: TAMU School of Veterinarian Medicine) at a level calculated to be LD 50. Mortality was assessed at day three (3) and day seven (7) following inoculation.

Figure 8:
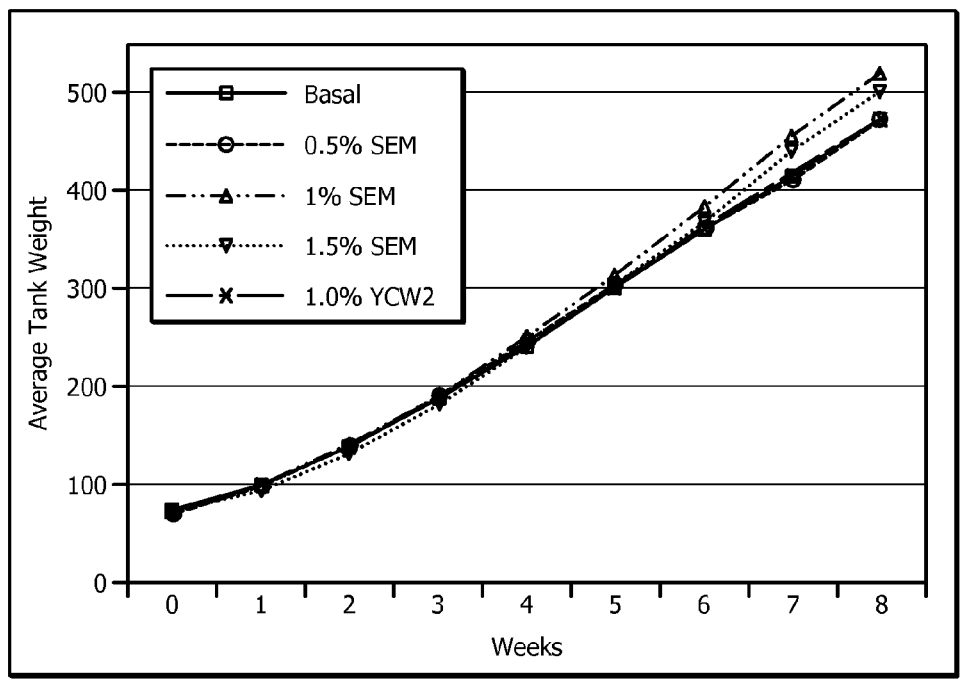
FIG. 8 is a graph illustrating cumulative tank weight through 8 weeks.
Figure 9:
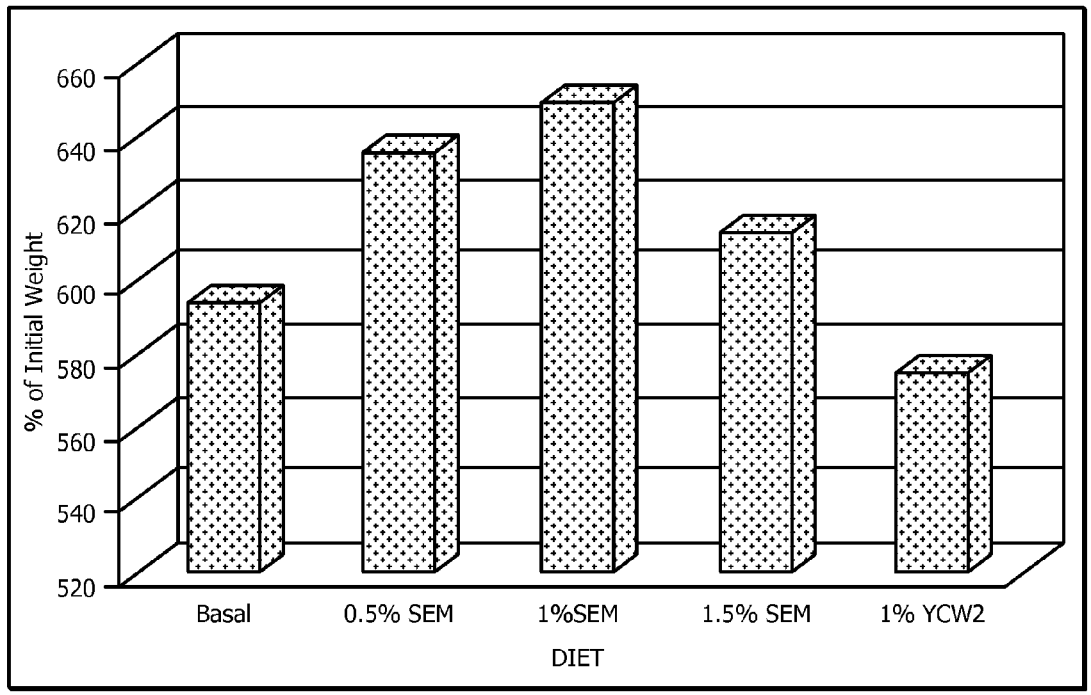
FIG. 9 is a graph illustrating total % weight through 8 weeks.
Figure 10:
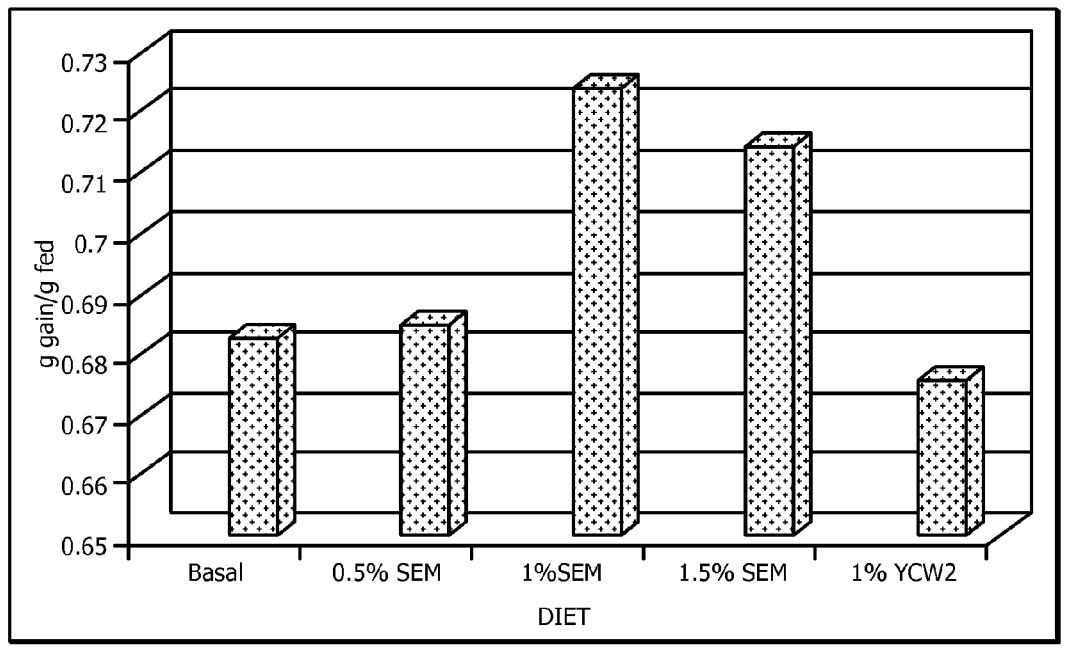
FIG. 10 is a graph illustrating Hybrid Striped Bass feed efficiency of diets.

Cumulative weight gain (mean tank weights) demonstrated a positive diverging trend during the feeding period for diets containing 1% and 1.5% SEM (FIG. 8). Percent weight gain (percentage of initial weight) (FIG. 9) and feed efficiency (fish weight gain in grams per gram of diet fed) (FIG. 10) were also numerically higher than the basal and yeast-based diet after the feeding period. Although whole-model significant differences among treatments were not detected through ANOVA, subsequent contrast analysis (Statistical Analysis Systems, Cary, N.C. General Linear Model Procedure), indicated significantly higher ($p=0.0709$) percent weight gain response of the 1% the prebiotic compared to diets with the 1% yeast-based product. Contrasts of raw tank weights (accounts for mortality) also indicated significantly higher weight gain for fish fed 1% the prebiotic as compared to the basal diet ($p=0.0562$) and fish diets containing the yeast-based product ($p=0.0523$).

Figure 11:
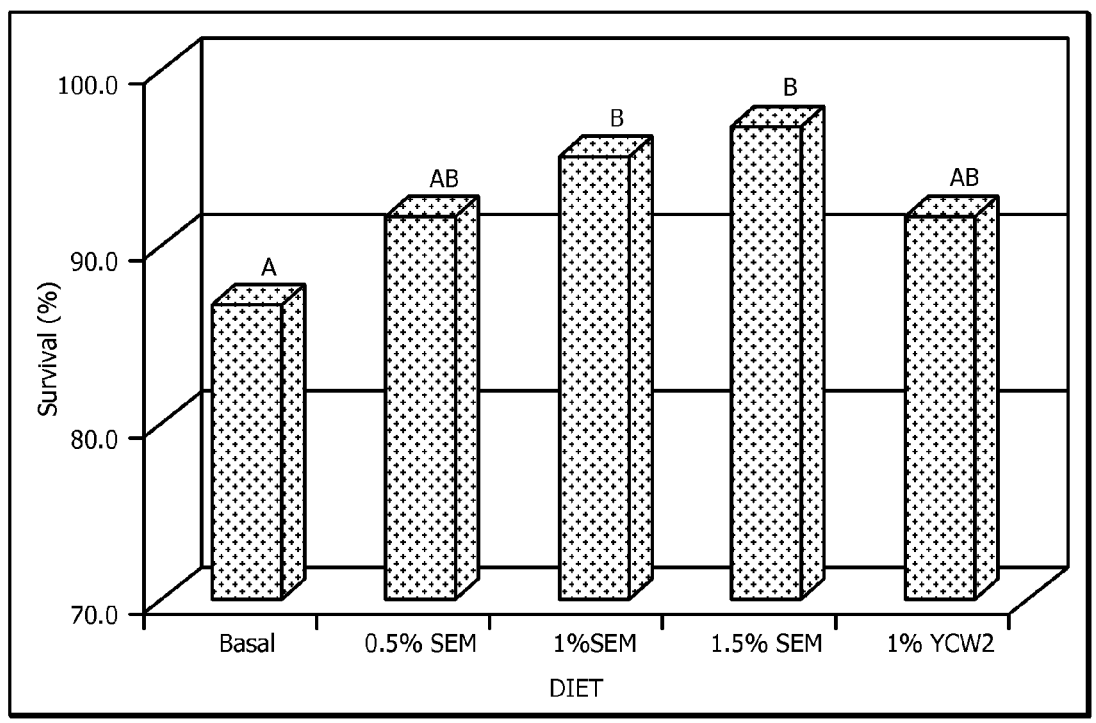
FIG. 11 is a graph illustrating Hybrid Striped Bass survival after week 8.

Following the 8 week feeding period, fish on diets with 1% and 1.5% SEM exhibited significantly higher survival ($p=0.0255$) than fish on the basal diet (FIG. 11).

Figure 12:
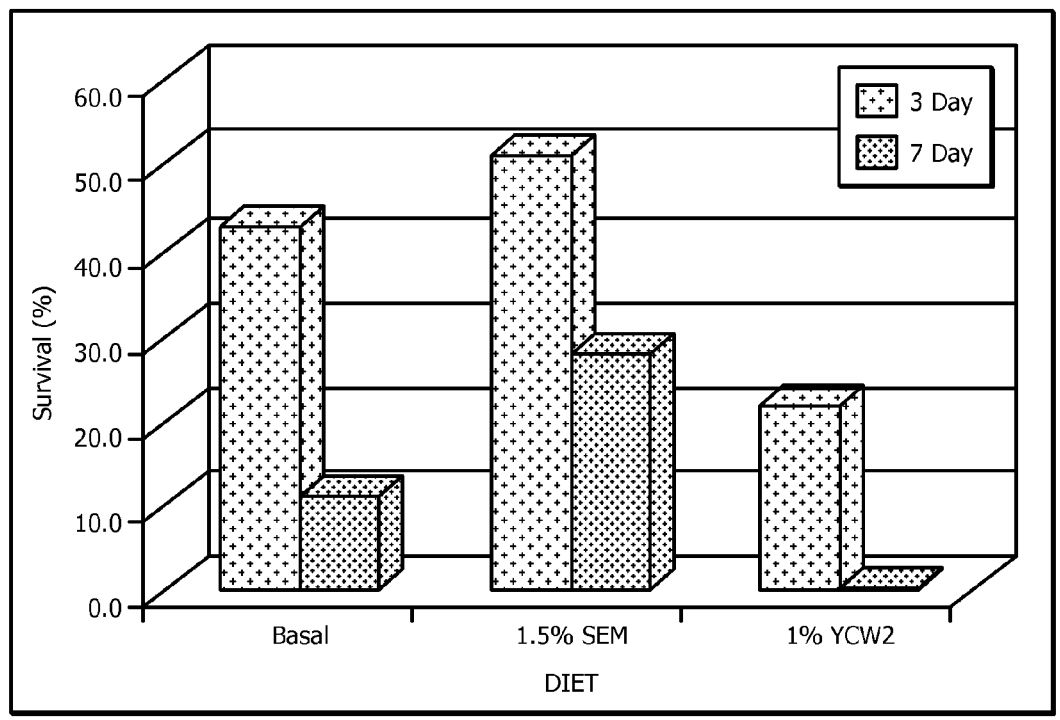
FIG. 12 is a graph illustrating Hybrid Striped Bass survival after *Streptococcus iniae* inoculation.

During the seven-day *Streplococcus* challenge period, fish on diets including 1.5% SEM had significantly higher ($p=0.0006$) survival at day 3 than fish on the diet with the yeast-based product, and significantly higher survival at day 7 ($p=0.0611$) than either the basal or yeast-based product diet (FIG. 12). These results indicate that the prebiotic (SEM) has the potential to improve weight gain, feed efficiency, and survival in aquaculture applications.

Example 3

A fifteen treatment shrimp feeding experiment was carried out with the SEM, a galactoglucomannan oligosaccharide of the type described herein. Diets with four different inclusion rates of the SEM, a basal control, and three competitive prebiotics were fed to shrimp in high population density (100 shrimp/tank) and low population density (20 shrimp/tank) production scenarios. The SEM has shown that it will perform equal to or better than competitive commercial prebiotic products in regard to growth and survival. Results indicate that the SEM has the potential to improve weight gain and survival in shrimp aquaculture applications. In particular, the SEM shows that it has potential for increase weight gain at low inclusion rates.

Example 4

Effects of Oligosaccharide Composition on Microbial Metabolism in Continuous Culture of Rumen Contents Procedures Lactation rations were formulated to support 45.5 kg of milk production per day. The test product was an SEM of the type described herein. The study comprised 4 treatments identified in the following manner:
1) Control Diet
2) Control Diet+0.25% SEM (SEM1)
3) Control Diet+0.50% SEM (SEM2)
4) Control Diet+1.00% SEM (SEM3)

The levels of SEM were added on a % DMR (dry matter ration) basis. Continuous culture fermentations were conducted using conditions simulating rumen parameters of a lactating dairy cow. Each diet was fermented in triplicate 9-day fermentations, with effluent samples composited for analysis during the last three days.

The addition of SEM to the diets appeared to have a disruptive effect on the structure of the polysaccharides, in that the digestion of NDF (neutral detergent fiber), ADF (acid detergent fiber) and NSC (non-structural carbohydrates) was significantly increased by at least one of the treatment levels. Digestion of ADF was increased by treatments SEM2 and SEM3. Compared to the control, digestion of NSC was improved slightly by SEM1 and SEM2, but was highest for SEM3. Digestion of NDF was increased by all levels of SEM, and was numerically highest for treatment SEM1, indicating a possible primary effect on digestion of hemicellulose. A summary of results is shown in Table 1.

TABLE 1

| | Digestion Coefficients (%) | | | | |
|---|---|---|---|---|---|
| | Control | 0.25* | 0.5* | 1.0* | P = |
| Dry matter | 61.8 | 65.9 | 68.7 | 68.6 | .046 |
| NDF | 36.9 | 44.3 | 42.2 | 40.0 | .116 |
| ADF | 33.3 | 31.5 | 44.5 | 38.6 | .032 |
| NSC | 76.2 | 81.0 | 78.7 | 83.5 | .043 |

*Percent of SEM in dry matter of digesta

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural or other details supplementary to the disclosure.

The invention claimed is:

1. A method of producing an orally-ingestible admixture in the form of a powder, a capsule, a tablet, a pellet, a nut, a nugget, an oil cake, a press cake, or a meal formulation, the method comprising:
providing a lignocellulosic source, wherein the lignocellulosic source comprises at least one species selected from the group consisting of *Pinus Zaeda* L. and its hybrids, *Pinus ellioli Englem* and its hybrids, *Pinus echinala* Mill and its hybrids, and *Pinus palustris* Mill and its hybrids;
extracting soluble materials from the lignocellulosic source to produce soluble extractable material, wherein the soluble extractable material comprises galactoglucomannans having glucose units, galactose units, and mannose units in a ratio of about 3 to about 1 to about 6; and
processing the soluble extractable material to yield a prebiotic composition, wherein the prebiotic composition exhibits prebiotic activity.

2. The method of claim 1, wherein extracting soluble material comprises softening the lignocellulosic source.

3. The method of claim 1, wherein softening of the lignocellulosic source comprises autohydrolysis, pulping, steam explosion, steam extrusion, or combinations thereof.

4. The method of claim 1, wherein the soluble extractable material comprises xylans, arabinoxylans, derivatives thereof or combinations thereof.

5. The method of claim 1 further comprising hydrolyzing the soluble extractable materials to produce a hydrolyzed composition.

6. The method of claim 5, wherein the hydrolyzed composition comprises polysaccharides having a degree of polymerization of from about 2 to about 20.

7. The method of claim 1 further comprising dehydrating the soluble extractable materials.

8. A method comprising administering the orally-ingestible admixture produced by the method of claim 1, to an organism for prophylactic treatment of a gastrointestinal ailment by stimulating growth and/or the activity of one or more beneficial microflora present within the organism's gastrointestinal tract.

* * * * *

UNITED STATES PATENT AND TRADEMARK OFFICE
CERTIFICATE OF CORRECTION

PATENT NO. : 9,301,540 B2
APPLICATION NO. : 12/480171
DATED : April 5, 2016
INVENTOR(S) : Anne Chace Hopkins et al.

Page 1 of 1

It is certified that error appears in the above-identified patent and that said Letters Patent is hereby corrected as shown below:

IN THE SPECIFICATION

Column 4, Line 43, replace "skill in the ari" with --skill in the art--

Columns 9-10, Lines 50-67 and Columns 11-12, lines 1-26, replace

"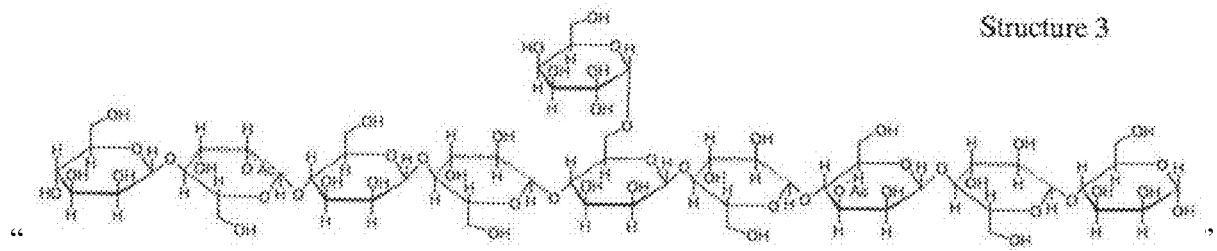"

with

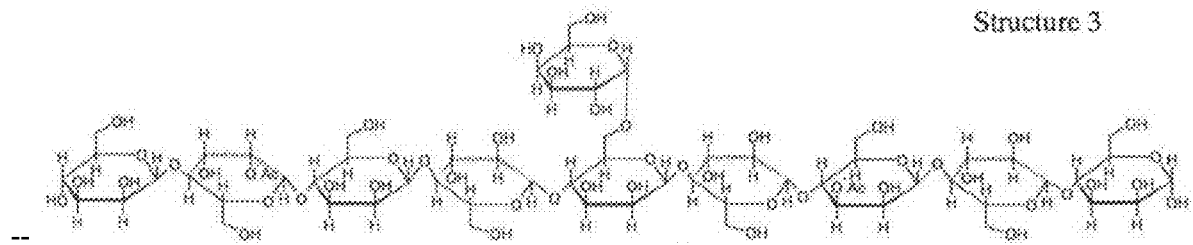

--

Signed and Sealed this
Twenty-first Day of June, 2016

Michelle K. Lee
*Director of the United States Patent and Trademark Office*